United States Patent [19]

Ueno

[11] Patent Number: 5,302,617
[45] Date of Patent: Apr. 12, 1994

[54] BIOCHEMICAL TREATMENT WITH 15-DEHYDROXY-16-OXOPROSTAGLANDIN COMPOUNDS

[75] Inventor: Ryuji Ueno, Hyogo, Japan

[73] Assignee: Kabushikikaisha Ueno Seiyaku Oyo Kenkyuio, Osaka, Japan

[21] Appl. No.: 932,690

[22] Filed: Aug. 20, 1992

Related U.S. Application Data

[63] Continuation-in-part of Ser. No. 691,289, Apr. 25, 1991, abandoned.

[30] Foreign Application Priority Data

Apr. 27, 1990 [JP] Japan .................................. 2-112303
Mar. 1, 1991 [JP] Japan .................................. 3-061327

[51] Int. Cl.$^5$ .................... A61K 31/19; A61K 31/557
[52] U.S. Cl. ...................................................... 514/573
[58] Field of Search ............................................ 514/573

[56] References Cited

U.S. PATENT DOCUMENTS

| | | | |
|---|---|---|---|
| 3,644,638 | 2/1972 | Rosenthale et al. | 424/305 |
| 3,836,667 | 9/1974 | Collier et al. | 424/318 |
| 4,128,720 | 12/1978 | Hayashi et al. | 560/9 |
| 4,170,709 | 10/1979 | Kao et al. | 560/121 |

FOREIGN PATENT DOCUMENTS

| | | |
|---|---|---|
| 0115419 | 8/1984 | European Pat. Off. . |
| 0153858 | 9/1985 | European Pat. Off. . |
| 0261798 | 3/1988 | European Pat. Off. . |
| 0391218 | 10/1990 | European Pat. Off. . |
| 0444844 | 2/1991 | European Pat. Off. . |
| 913014809 | 2/1991 | European Pat. Off. . |
| 0444844 | 9/1991 | European Pat. Off. . |
| 2217602 | 11/1989 | United Kingdom . |

OTHER PUBLICATIONS

*Chem. Abst.*, 90, 22371g (1979).
*Prostaglandins*, vol. 11, No. 2, Feb. 1976, pp. 227–239.
*Prostaglandins*, vol. 16, No. 3, Sep. 1978, pp. 461–465.

*Primary Examiner*—Frederick E. Waddell
*Assistant Examiner*—Raymond J. Henley, III
*Attorney, Agent, or Firm*—Sughrue, Mion, Zinn, Macpeak & Seas

[57] ABSTRACT

A method for treatment of an allergic disease which comprises administering, to a subject in need of such treatment, a 15-dehydroxy-16-oxoprostaglandin compound in an amount effective in treatment of the allergic disease

26 Claims, No Drawings

BIOCHEMICAL TREATMENT WITH 15-DEHYDROXY-16-OXOPROSTAGLANDIN COMPOUNDS

This application is a continuation-in-part of U.S. patent application Ser. No. 07/691,289, filed on Apr. 25, 1991 now abandoned.

BACKGROUND OF THE INVENTION

1. Field of the Invention

The present invention relates to a method for treatment of allergic diseases, inflammatory diseases, diseases treatable by an antihistaminic agent, diseases treatable by a leukotriene antagonist, diseases treatable by a platelet activating factor antagonist and diseases treatable by bronchodilatation which comprises administering a 15-dehydroxy-16-oxoprostaglandin compound to a subject.

Nowadays, it is well established that histamine is acting as a chemical mediator in allergic and inflammatory diseases. Leukotrienes, compounds known as the slow reacting substances (SRS), are also known to be mediators in various biological reactions. Furthermore, it has recently been demonstrated that the slow reacting substances (SRS) such as leukotrienes involve in autoimmune diseases (AID). Also, the platelet activating factor (PAF) is being accepted as a chemical mediator in allergic and inflammatory reactions.

Presently, antihistaminic agents are widely used in the treatment of various allergic and inflammatory diseases. Although anti-lipoxigenases, substances inhibiting production of leukotrienes, and platelet activating factor antagonists have also been attempted in treatment of these disease, satisfactory results have not been obtained.

Prostaglandins (hereinafter, prostaglandins are referred to as PGs) are members of a class of organic carboxylic acid that are contained in human and most other mammalian tissues or organs and that exhibit a wide range of physiological activities. Naturally occurring PGs possess as a common structural feature the prostanoic acid skeleton:

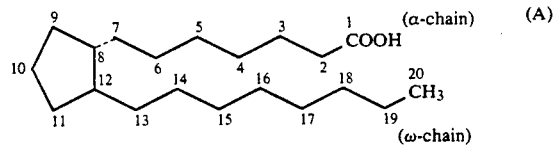

Some synthetic analogues have somewhat modified skeletons. The primary PGs are classified based on the structural feature of the five-membered cycle moiety into PGAs, PGBs, PGCs, PGDs, PGEs, PGFs, PGGs, PGHs, PGIs and PGJs, and also on the presence or absence of unsaturation and oxidation in the chain moiety as:

| | |
|---|---|
| Subscript 1 | 13,14-unsaturated-15-OH |
| Subscript 2 | 5,6- and 13,14-diunsaturated-15-OH |
| Subscript 3 | 5,6- 13,14- and 17,18-triunsaturated-15-OH |

Further, PGFs are sub-classified according to the configuration of hydroxy group at position 9 into α(hydroxy group being in the alpha configuration) and μ (hydroxy group being in the beta configuration).

2. Background Information

Some 15-dehydroxy-16-oxoprostaglandin compounds are disclosed in Japanese patent application No. 55930/1991 (U.S. patent application No. 660,833/07, European patent application No. 91301480.9).

As stated above, the activities of the primary PGs are diversified an one compound has various activities coexistently. While the fact that a compound has various activities appears to be advantageous at first sight, the presence of activities which are not useful in individual cases is not desirous because they are disliked as side-effects. Therefore, it is desirous to develop compounds having only one particular activity or a limited number of activities out of various activities of PGs. Furthermore, there is a continuous demand for the compounds of this kind which have improved chemical stability and reduced rate of metabolic degradation in the living body in comparison with the natural PGs. It has now been found that, as a results of extensive study seeking for such compounds, 15-dehydroxy-16-oxoprostaglandin compounds have excellent activities such as antiallergic, antiinflammatory, antihistaminic, leukotriene-antagonistic, platelet activating factor antagonistic and bronchodilatative activities.

SUMMARY OF THE INVENTION

In a first aspect, the present invention provides a method for treatment of an allergic disease which comprises administering, to a subject in need of such treatment, a 15-dehydroxy-16-oxoprostaglandin compound in an amount effective in treatment of the allergic disease.

In another aspect, the present invention provides a method for treatment of an inflammatory disease which comprises administering, to a subject in need of such treatment, a 15-dehydroxy-16-oxoprostaglandin compound in an amount effective in treatment of the inflammatory disease.

In another aspect, the present invention provides a method for treatment of a disease treatable by an antihistaminic agent which comprises administering, to a subject in need of such treatment, an antihistaminically effective amount of a 15-dehydroxy-16-oxoprostaglandin compound.

In another aspect, the present invention provides a method for treatment of a disease treatable by a leukotriene antagonist which comprises administering, to a subject in need of such treatment, a 15-dehydroxy-16-oxoprostaglandin compound in an amount effective in antagonism against a leukotriene.

In another aspect, the present invention provides a method for treatment of a disease treatable by a platelet activating factor antagonist which comprises administering, to a subject in need of such treatment, a 15-dehydroxy-16-oxoprostaglandin compound in an amount effective in antagonist against the platelet activating factor.

In another aspect, the present invention provides a method for treatment of a disease treatable by bronchodilatation which comprises administering, to a subject in need of such treatment, a 15-dehydroxy-16-oxoprostaglandin compound in an amount effective in causing bronchodilatation.

In a further aspect, the present invention provides a use of a 15-dehydroxy-16-oxoprostaglandin compound for the manufacture of a medicament for treatment of an allergic disease.

In another aspect, the present invention provides a use of a 15-dehydroxy-16-oxoprostaglandin compound for the manufacture of a medicament for treatment of an inflammatory disease.

In another aspect, the present invention provides a use of a 15-dehydroxy-16-oxoprostaglandin compound for the manufacture of a medicament for treatment of a disease treatable by an antihistaminic agent.

In another aspect, the present invention provides a use of a 15-dehydroxy-16-oxoprostaglandin compound for the manufacture of a medicament for treatment of a disease treatable by an leukotriene antagonist.

In another aspect, the present invention provides a use of a 15-dehydroxy-16-oxoprostaglandin compound for the manufacture of a medicament for treatment of a disease treatable by an platelet activating factor antagonist.

In another aspect, the present invention provides a use of a 15-dehydroxy-16-oxoprostaglandin compound for the manufacture of a medicament for treatment of a disease treatable by an bronchodilatation.

In a still further aspect, the present invention provides a pharmaceutical composition for treatment of an allergic disease comprising, a 15-dehydroxy-16-oxoprostaglandin compound in association with a pharmaceutically acceptable carrier, diluent or excipient.

In another aspect, the present invention provides a pharmaceutical composition for treatment of an inflammatory disease comprising a 15-dehydroxy-16-oxoprostaglandin compound in association with a pharmaceutically acceptable carrier, diluent or excipient.

In another aspect, the present invention provides a pharmaceutical composition for treatment of a disease treatable by an antihistaminic agent comprising a 15-dehydroxy-16-oxoprostaglandin compound in association with a pharmaceutically acceptable carrier, diluent or excipient.

In another aspect, the present invention provides a pharmaceutical composition for treatment of a disease treatable by a leukotriene antagonist comprising a 15-dehydroxy-16-oxoprostaglandin compound in association with a pharmaceutically acceptable carrier, diluent or excipient.

In another aspect, the present invention provides a pharmaceutical composition for treatment of a disease treatable by a platelet activating factor antagonist comprising a 15-dehydroxy-16-oxoprostaglandin compound in association with a pharmaceutically acceptable carrier, diluent or excipient.

In another aspect, the present invention provides a pharmaceutical composition for treatment of a disease treatable by bronchodilation comprising a 15-dehydroxy-16-oxoprostaglandin compound in association with a pharmaceutically acceptable carrier, diluent or excipient.

DETAILED DESCRIPTION OF THE INVENTION

The term "allergic disease" refers to a disease based on a reaction detrimentally acting on a living body and caused, on second explosure to a particular substance (antigen or allergen, such as pollen, grain flour, dust, animal air-borne substances, foods, drugs, therapeutic sera, bacteria and products thereof, etc.), by antibodies formed by allergic reaction, i.e. elicited through exposure to said substance. Said disease includes hay fever (seasonal nasal catarrh or vasomotor rhinitis), bronchial asthma, serum sickness, serum shock, allergic dematilis, allergic gastritis, allergic arthritis, allergic conjunctivitis, allergic diarrhea, allergic laryngitis, allergic purpurea (Schoenlein-Henoch purpurea), allergic neuritis, allergic granulomatosis, allergic encephalomyelitis, allergic alveolitis, allergic nephritis, allergic rhinitis, allergic asthma, allergic eczema, etc.

Further, in the present invention, it includes diseases, known as autoimmune diseases, characterized by tissue disorder caused against cells of "self" by the production of antibodies reactive to substances forming the tissue of "self". Such diseases include rheumatoid arthritis (RA), systemic lupus erythematosus (SLE) progressive systemic sclerosis (PSS), Hashimoto's disease, Sjoegren syndrome, hyperthroidism, myasthenic syndrome, Behet disease, etc.

The term "inflammatory disease" means lesions comprising circulatory disorder, exudation, degeneration, hyperplasia, etc. caused by inflammatory reaction, i.e. induced by (physical, chemical, microbial and other parasitic) stimulation which may destroy the dynamic equilibrium in the function or structure of local organ or tissue of living body and have signs of redness, heat, pain, swelling and loss of function. Said disease includes conjunctivitis, iritis, uveitis, central retinitis, external otitis, acute suppurative otitis media, mastoiditis, labyrinthitis, chronic rhinitis, acute rhinitis, sinusitis, pharyngitis, tonsillitio, chronic bronchitis, acute bronchilotis, lobar pneumonia, bronchopneumonia, primary atypical pneumonia, dry pleurisy, wet pleurisy, mediastinitis, acute rheumatic endocarditis, bacterial endocarditis, thrombophlebitis, polyarteritis, acute nephritis, chronic nephritis, cystitis, paranephlitis, stomatitis, esophagitis, acute gastritis, chronic gastritis, ulcertive colitis, acute appendicitis, chronic hepatitis, acute hepatitis, cholangiolitic hepatitis, cholecysititis, chronic pancreatitis, acute pancreatitis, chronic peritonitis, acute peritonitis, thyroiditis, contact dermatitis, acute hemorrhagic encephalitis, purulent meningitis, optic neuromyelitis, alcoholic polyneuritis, diabetic polyneuritis, polymyositis, myositis ossificans, degenerative arthritis, rheumatoid arthritis, periarthritis scapulohumeralis, osteitis deformans, etc.

Histamine is a substance occurring in many animal and human tissues but particularly in the granules of mast cells and basophils, released in response to nonimmune stimulation (traumatic or toxic stimulation, or stimulation with certain compounds such as Compound 48/80) or immune stimulation and inducing allergic symptoms such as itching, edema, redness, bronchial constriction, etc.

Leukotrienes (LTs) refer to chemical mediators of inflammation formed in leukocyte or macrophage, having three conjugated double bonds, biosysnthesized through the same passage as that for prostaglandins and classified to A, B, C, D, E and analogues. These have a strong action of constricting smooth muscles (particularly bronchial muscle), action of increasing airway resistance, promoting tracheal mucomembranous secretion and increasing capillary permeability, leukocyte migration and leukocyte agglutination etc. The substance known as SRS-A, released on inflammation, is a mixture of $LTC_4$ and $LTD_4$.

Platelet activating factor (PAF) is a phospholipid, causing activation of neutrophile, macrophage and platelet, and released from neutrophile and renal interstitial cells in response to stimulation of inducing substances. Its biosynthetic precursor is common with arachidonic acid. This substance has, in addition to the above activating functions, action of increasing capillary permeability and promoting smooth muscle constriction, drop in blood pressure and glycogenolysis in liver and mediates inflammation or anaphylaxis.

Bronchial smooth muscle constricts by stimulation of histamine receptor or leukotriene receptor. It also constricts by attaching of acetylcholine, released from peripheral parasympathetic nerve upon stimulation, to cholinegic receptor on the surface of the smooth muscles. When sympathethic nerve is stimulated, smooth muscles relax by stimulation of their -receptors with noradrenaline released from peripheral sympathetic nerve or adrenaline released from adrenal medullary, while they constrict on stimulation of their α-receptors. Any agents having activity of directly or indirectly inhibiting or blocking the above illustrated mechanism of constriction are included in agents causing bronchodilation.

As used herein, the term "treatment" or "treating" refers to any means of control of a disease in a mammal, including preventing the disease, curing the disease, relieving the disease and arresting or relieving the development of the disease.

The term "15-dehydroxy-16-oxoprostaglandin compounds", referred to as 15-dehydroxy-16-oxo-PG compounds, include prostaglandin derivatives which lack the hydroxy group at position 15 and have an oxo group at position 16 of the prostanoic acid nucleus irrespective of the presence or absenceof unsaturation (double or triple bond).

Nomenclature

Nomenclature of 15-dehydroxy-16-oxo-PG compounds herein uses the numbering system of prostanoic acid represented in formula (A) shown above.

While formula (A) shows a basic skeleton having twenty carbon atoms, the 15-dehydroxy-16-oxo-PG compounds used in the present invention are not limited to those having the same number of carbon atoms. The carbon atoms in Formula (A) are numbered 2 to 7 on the α-chain starting from the α-carbon atom adjacent to the carboxylic carbon atom which is numbered 1 and towards the five-membered ring, 8 to 12 on the said ring starting from the carbon atom on which the α-chain is attached, and 13 to 20 on the ω-chain starting from the carbon atom adjacent to the ring. When the number of carbon atoms is decreased in the α-chain, the number is deleted tin order starting from position 2 and when the number of carbon atoms is increased in the α-chain, compounds are named as substituted derivatives having respective substituents at position 1 in place of carboxy group (C-1). Similarly, when the number of carbon atoms is decreased in the ω-chain, the number is deleted in order starting from position 20 and when the number of carbon atoms is increased in the ω-chain, compounds are named as substituted derivatives having respective substituents at position 20. Stereochemistry of the compounds is the same as that of above formula (A) unless otherwise specified. Thus, 15-dehyroxy-16-oxo-PG compounds having 10 carbon atoms in the ω-chain is nominated as 15-dehydroxy-16-oxo-20-ethyl-PGs.

The above formula expresses a specific configuration which is the most typical one, and in this specification compounds having such a configuration are expressed without any specific reference to it.

In general, PGDs, PGEs and PGFs have a hydroxy group on the carbon atom at position 9 and/or 11 but in the present specification the term "15-dehydroxy-16-oxo-PG compounds" includes PGs having a group other than a hydroxyl group at position 9 and/or 11. Such PGs are referred to as 9-dehydroxy-9-substituted-PG compounds or 11-dehydroxy-11-substituted-PG compounds.

As stated above, nomenclature of 15-dehydroxy-16-oxo-PG compounds is based upon the prostanoic acid. These compounds, however, can also be named according to the IUPAC naming system. Some example of these nomenclatures are shown in the Preparation Examples.

Preferred Compounds

The 15-dehydroxy-16-oxo-PG compounds used in the present invention may be any derivatives of PG insofar as they lack the hydroxy group at position 15 and have an oxo group at position 16, and may have a double bond between positions 13 and 14 (15-dehydroxy-16-oxo-PG subscript 2 compounds), or three double bonds between positions 13 and 14, positions 5 and 6 as well as positions 17 and 18 (15-dehydroxy-16-oxo-PG subscript 3 compounds), and may have a single bond between positions 13 and 14 (13,14-dihydro-15-dehydroxy-16-oxo-PG compounds).

Typical examples of the compounds used in the present invention are 15-dehydroxy-16-oxo-PGA, 15-dehydroxy-16-oxo-PGD, 15-dehydroxy-16-oxo-PGE, 15-dehydroxy-16-oxo-PGF, 13,14-dihydro-15-dehydroxy-16-oxo-PGA, 13,14-dihydro-15-dehydroxy-16-oxo-PGD, 13,14-dihydro-15-dehydroxy-16-oxo-PGE, and 13,14-dihydro-15-dehydroxy-16-oxo-PGF, wherein PG is as defined above as well as their substitution products or derivatives.

Examples of substitution products or derivatives include esters at the carboxy group at the alpha chain, pharmaceutically or physiologically acceptable salts, unsaturated derivatives having a double bond or a triple bond between positions 2 and 3 or positions 5 and 6, respectively, substituted derivatives having substituent(s) on carbon atom(s) at position 3, 5, 6, 16, 18, 19 and/or 20 and compounds having lower alkyl or a hydroxy (lower) alkyl group at position 9 and/or 11 in place of the hydroxy group, of the above PGs.

Examples of substituents present in preferred compounds are as follows: Substituents on the carbon atom at position 3, 18 and/or 19 include lower alkyl, for example, $C_{1-4}$ alkyl, especially methyl and ethyl. Substituents on the carbon atom at position 17 include lower alkyl e.g. methyl, ethyl etc., hydroxy and halogen atom e.g. chlorine, fluorine, aryloxy e.g. trifluoromethylphenoxy, etc. Substituents on the carbon atom at position 18 include halogen atom e.g. chlorine, fluorine etc. Substituents on the carbon atom at position 20 include saturated and unsaturated lower alkyl e.g. $C_{1-4}$ alkyl, lower alkoxy e.g. $C_{1-4}$ alkoxy and lower alkoxy (lower) alkyl e.g. $C_{1-4}$ alkoxy-$C_{1-4}$ alkyl. Substituents on the carbon atom at position 5 include halogen atom e.g. chlorine, fluorine etc. Substituents on the carbon atom at position 6 include oxo group forming carbonyl. Stereochemistry of PGs having hydroxy, lower alkyl or lower (hydroxy) alkyl substituent on the carbon atom at position 9 and/or 11 may be alpha, beta or mixtures thereof.

Said derivatives may have an alkoxy, phenoxy or phenyl group at the end of the omega chain where the chain is shorter than the primary PGs.

Especially preferred compounds are those having a lower alkyl e.g. methyl, ethyl etc., a halogen atom e.g. chloro, fluoro etc. at position 17, those having a halogen atom e.g. chloro, fluoro etc. at position 18, those having a lower alkyl e.g. methyl, ethyl etc. at position 20, those having a halogen atom e.g. chlorine, fluorine etc. at position 5, those having an oxo group at position 6, those having a lower alkyl, e.g. methyl, ethyl, etc. at position 19 and those having phenyl or phenoxy which are optionally substituted with halogen or haloalkyl at position 17 in place of the rest of the alkyl chain.

A group of preferred compounds used in the present invention has the formula

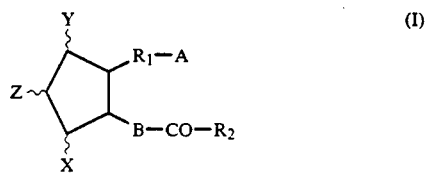

wherein X and Y are hydrogen, hydroxy, halo, lower alkyl, hydroxy(lower)alkyl, or oxo, with the proviso that at least one of X and Y is a group other than hydrogen, and 5-membered ring may have at least one double bond, Z is hydrogen or halo, A is —CH$_2$OH, —COCH$_2$OH, —COOH or its functional derivative, B is —CH$_2$—CH$_2$—CH$_2$—, —CH=CH—CH$_2$—, —CH$_2$—CH=CH—, —≡C—CH$_2$—or —CH$_2$—C≡C—, R$_1$ is bivalent saturated or unsaturated, lower or medium aliphatic hydrocarbon residue which is unsubstituted or substituted with halo, oxo or aryl, R$_2$ is saturated or unsaturated, lower or medium aliphatic hydrocarbon residue which is unsubstituted or substituted with halo, hydroxy, oxo, lower alkoxy, lower alkanoyloxy, cyclo(lower)alkyl, aryl or aryloxy.

In the above formula, the term "unsaturated" in the definitions for R$_1$ and R$_2$ is intended to include at least one and optionally more than one double bond and/or triple bond isolatedly, separately or serially present between carbon atoms of the main and/or side chains. According to usual nomenclature, an unsaturation between two serial positions is represented by denoting the lower number of said two positions, and an unsaturation between two distal positions is represented by denoting both of the positions. Preferred unsaturation is a double bond at position 2 and a double or triple bond at position 5.

The term "lower or medium aliphatic hydrocarbon residue" refers to a straight or branched chain hydrocarbyl group having 1 to 14 carbon atoms (for a side chain, 1 to 3 carbon atoms being preferred) and preferably 2 to 8 carbon atoms for R$_1$ and 2 to 10 carbon atoms for R2.

The term "halo" denotes fluoro, chloro, bromo and iodo.

The term "lower" throughout the specification is intended to include a group having 1 to 6 carbon atoms unless otherwise specified.

The term "lower alkyl" as a group or a moiety in hydroxy(lower)alkyl includes saturated and straight or branched chain hydrocarbon radicals containing 1 to 6, carbon atoms, e.g. methyl, ethyl, propyl, isopropyl, butyl, isobutyl, t-butyl, pentyl and hexyl.

The term "lower alkoxy" refers to the group lower-alkyl-0- wherein lower alkyl is as defined above.

The term "hydroxy(lower)alkyl" refers to lower alkyl as defined above which is substituted with at least one hydroxy group, e.g. hydroxymethyl, 1-hydroxyethyl, 2-hydroxyethyl and 1-methyl-1-hydroxyethyl.

The term "lower alkanoyloxy" refers to a group of the formula: RCO—O—wherein RCO— is an acyl group formed by oxidation of a lower alkyl group as defined above, e.g. acetyl.

The term "cyclo(lower)alkyl" refers to a cyclic group formed by cyclization of a lower alkyl group as defined above.

The term "aryl" includes unsubstituted or substituted aromatic carbocyclic or heterocyclic (preferably monocyclic) groups, e.g. phenyl, tolyl, xylyl and thienyl. Examples of substituents are halo and halo(lower)alkyl wherein halo and lower alkyl being as defined above.

The term "aryloxy" refers to a group of the formula: ArO- wherein Ar is aryl as defined above.

The term "functional derivative" of carboxy as A includes salts (preferably pharmaceutically acceptable salts), esters and amides.

Suitable "pharmaceutically acceptable salts" includes conventional non-toxic salts, and may be a salt with an inorganic base, for example an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)ethane salt, monomethyl-monoethanolamine salt, procaine salt, caffeine salt, etc.), a basic amino acid salt (e.g. arginine salt, lysine salt, etc.), tetraalkyl ammonium salt and the like. These salts can be prepared by the conventional process, for example from the corresponding acid and base or by salt interchange.

Examples of the esters are aliphatic esters, for example, lower alkyl ester e.g. methyl ester, ethyl ester, propyl ester, isopropyl ester, butyl ester, isobutyl ester, t-butyl ester, pentyl ester, 1-cyclopropylethyl ester, etc., lower alkenyl ester e.g. vinyl ester, allyl ester, etc., lower alkynyl ester e.g. ethynyl ester, propynyl ester, etc., hydroxy(lower) alkyl ester e.g. hydroxyethyl ester, lower alkoxy(lower)-alkyl ester e.g. methoxymethyl ester, 1-methoxyetyl ester, etc., and aromatic esters, for example, optionally substituted aryl ester e.g. phenyl ester, tosyl ester, t-butylphenyl ester, salicyl ester, 3,4-di-methoxy-phenyl ester, benzamidophenyl ester etc., aryl(lower)alkyl ester e.g. benzyl ester, trityl ester, benzhydryl ester, etc. Examples of the amides are mono- or di- lower alkyl amides e.g. methylamide, ethylamide, dimethylamide, etc., arylamide e.g. anilide, toluidide, and lower alkyl- or aryl-sulfonylamide e.g. methylsulfon-ylamide, ethylsulfonyl-amide, tolylsulfonylamide etc.

Preferred examples of A include —COOH, —COOCH$_3$, —COOCH$_2$CH$_3$, —COOCH(CH$_3$)$_2$ and —CONHSO$_2$CH$_3$.

The configuration of the ring and the α- and/or omega chain in the above formula (I) may be the same as or different from that in the primary PGs. However, the present invention also includes a mixture of a compound having a primary configuration and that of an unprimary configuration.

Examples of the typical compounds of the present invention are 15-dehydroxy-16-oxo-PGEs, 13,14-dihydro-15-dehydroxy-16-oxo-PGEs and their e.g. 6-oxo-derivatives, $\Delta^2$-derivatives, 3 R,S-methyl-derivatives, 5 R,S-fluoro-derivatives, 5,5-difluoro-derivatives, 17 R,S-methyl-derivatives, 17,17-dimethyl-derivatives, 17 R,S-fluoro-derivatives, 17,17-difluoro-derivatives, 18S-methyl-derivatives, 18 R,S-fluoro-derivatives, 18,18-difluoro-derivatives, 19-methyl-derivatives, 20-methyl-derivatives, 20-ethyl-derivatives, as well as 15-dehydroxy-16-oxo-PGFs, 13,14-dihydro-15-dehydroxy-16-oxo-PGFs, 15-dehydroxy-16-oxo-PGDs, 13,14-dihydro-15-dehydro-15-dehydroxy-16-oxo-PGDs, 15-dehydroxy-16-oxo-PGAs, 13,14-dihydro-15-dehydroxy-16-oxo-PGAs and their 17-despropyl-17-trifluoromethylphenoxy derivatives.

When 15-dehydroxy-16-oxo-PG compounds of the present invention have a saturated bond between positions 13, 14 and 15, these compounds may be in the keto-hemiacetal equilibrium by forming a hemiacetal between hydroxy group at position 11 and ketone at position 16.

The proportion of both tautomeric isomers, when present, varies depending on the structure of the rest of the molecule or kind of any substituent present and, sometimes, one isomer may predominantly be present in comparison with the other. However, in this invention, it is to be appreciated that the compounds used in the invention include both isomers. Further, while the compounds used in the invention may be represented by a structure or name based on keto-form regardless of the presence or absence of the isomers, it is to be noted that such structure or name does not intend elimination of the hemiacetal type of compounds.

In the present invention, any of the individual tautomeric isomers, a mixture thereof, or optical isomers, a mixture thereof, a racemic mixture, and other isomers such as steric isomers can be used in the same purpose.

Some of the compounds used in the present invention may be prepared by the method disclosed in Japanese patent application No. 55930/1991.

Alternatively, these compounds may be prepared by a process analogous to that described herein or to known processes.

A practical preparation of the 15-dehydroxy-16-oxo-PG compounds involves the following steps, wherein $P_1$, $P_2$, $P_3$, $P_4$, $P_5$, $P_6$, $P_7$, $P_8$, $P_9$, $P_{10}$, $P_{11}$ and $P_{12}$ are each protective group, L is a leaving group, $R_1'$ is —CH=CH—, X' is lower alkyl, A' is lower alkyl or monocyclic aryl(lower)alkyl, $Q_1$ and $Q_2$ are H or halo, and $R_2'$ is a group formed by removing >C($Q_1$,$Q_2$) from $R_2$.

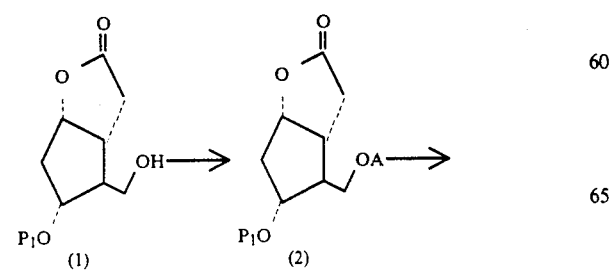

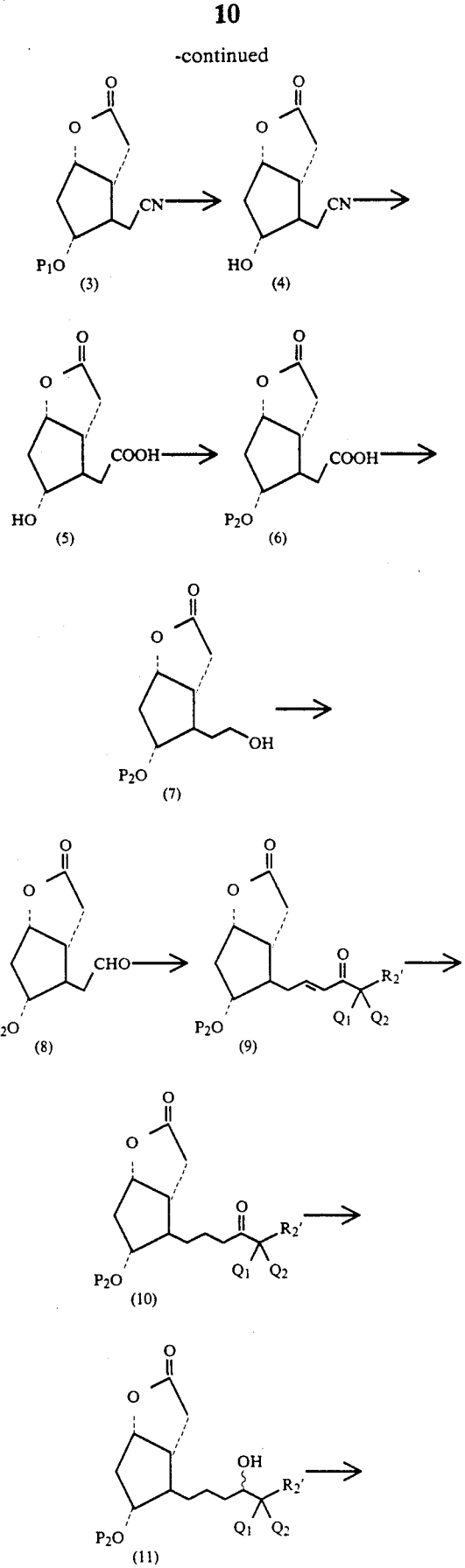

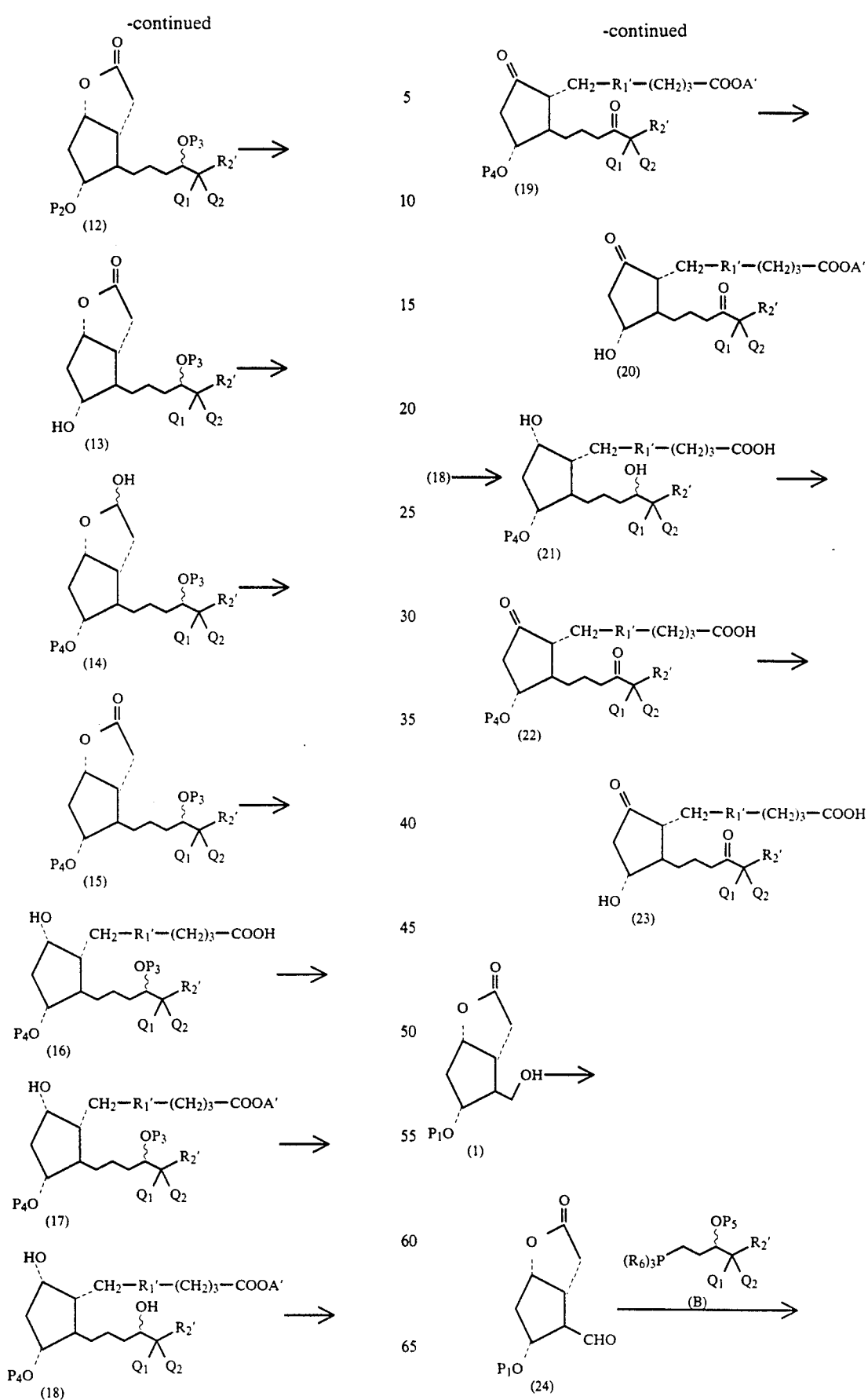

-continued
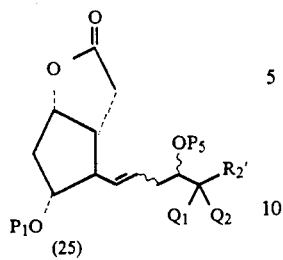
(25)
(13) →
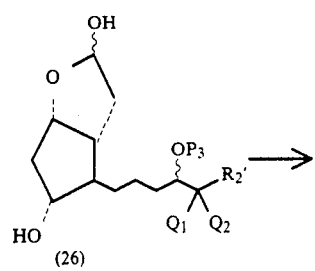
(26)
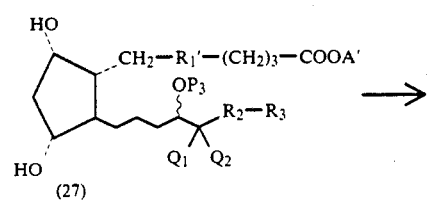
(27)
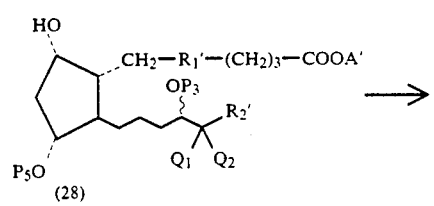
(28)
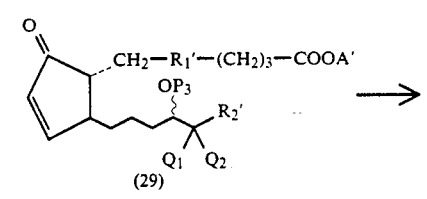
(29)
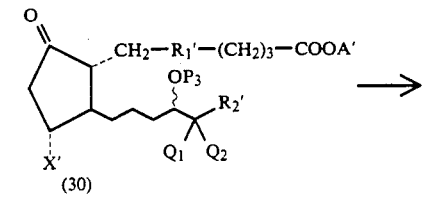
(30)
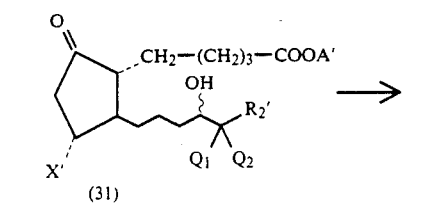
(31)
-continued
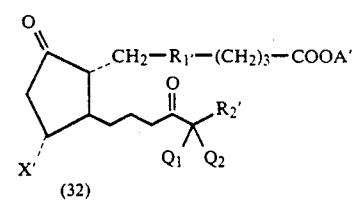
(32)
(18) →
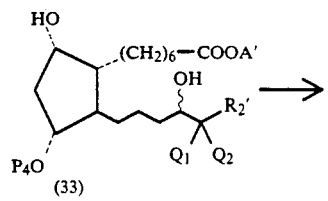
(33)
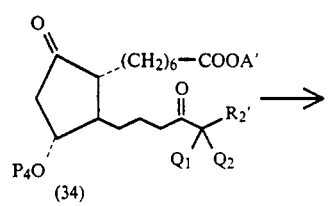
(34)
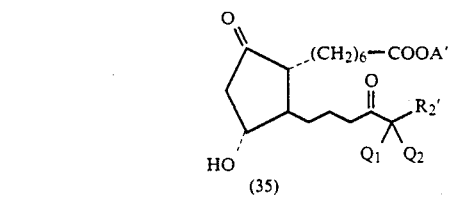
(35)
(13) →
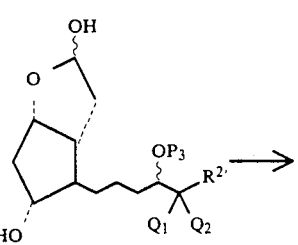
(36)
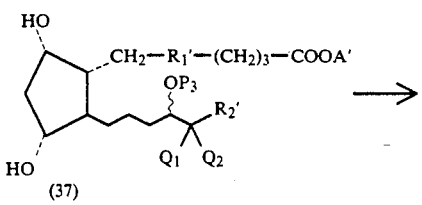
(37)
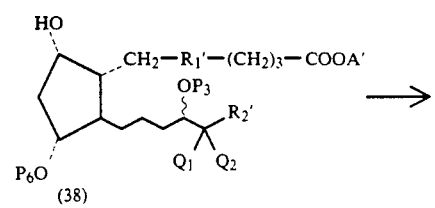
(38)

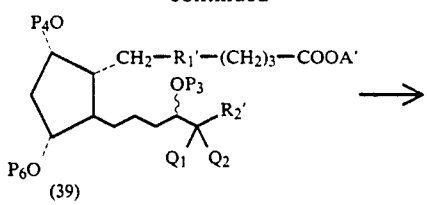
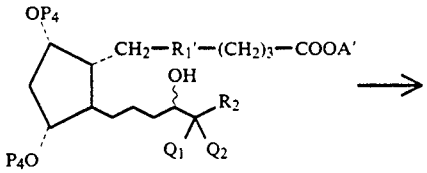
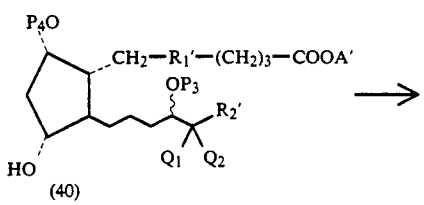
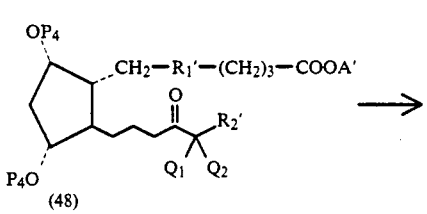
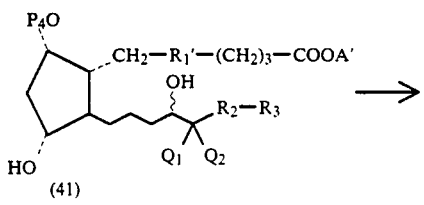
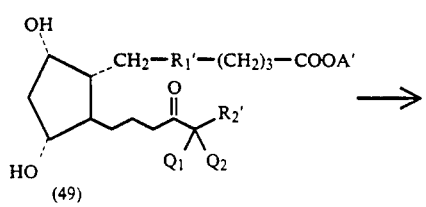
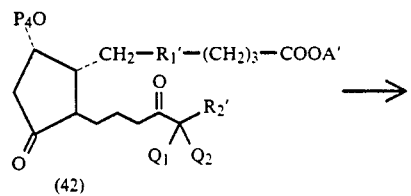
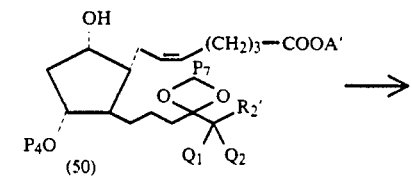
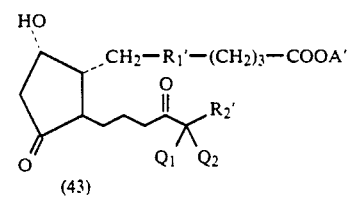
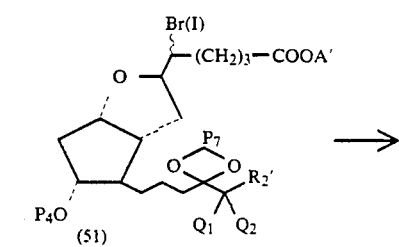
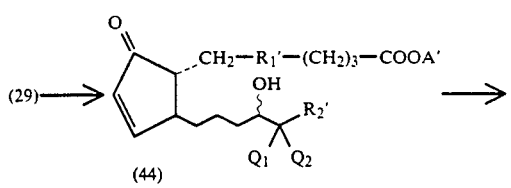
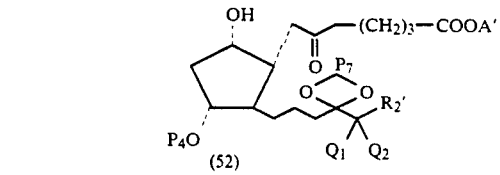
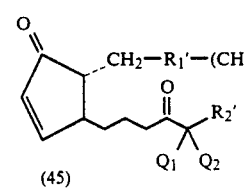
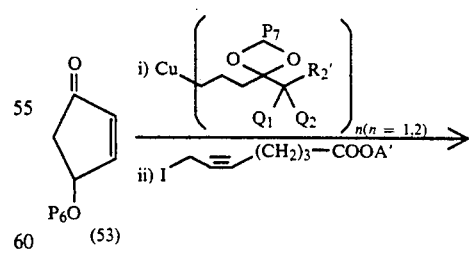
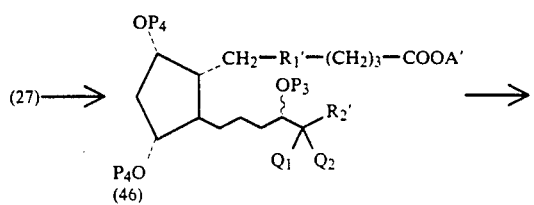
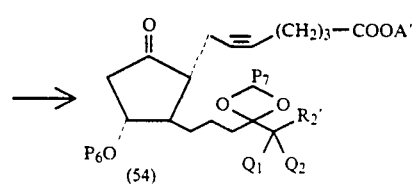

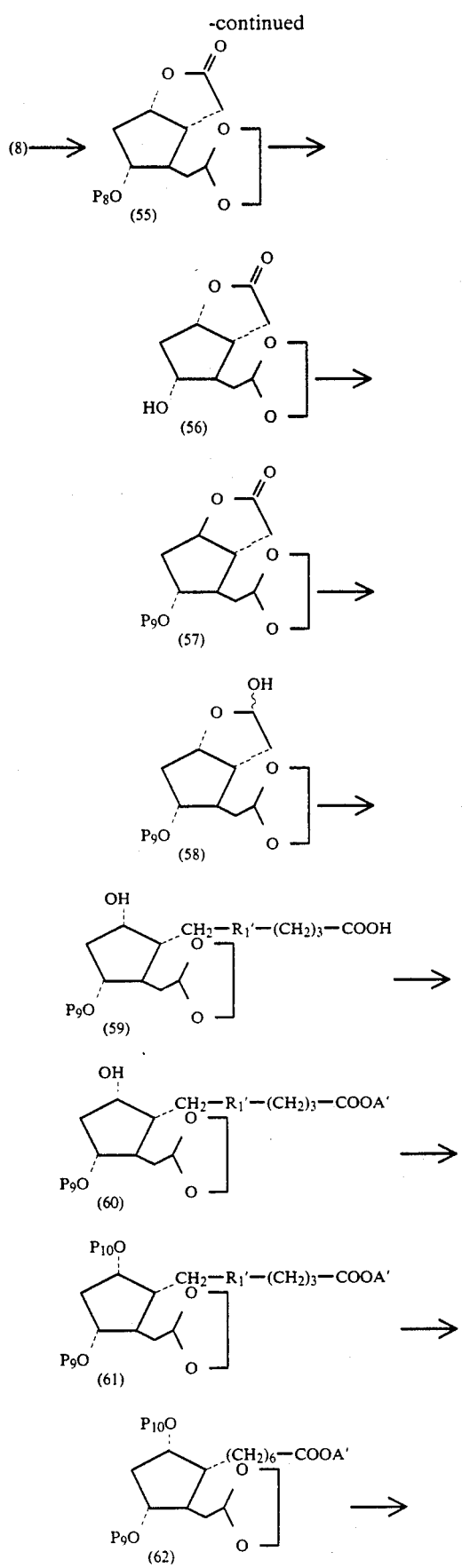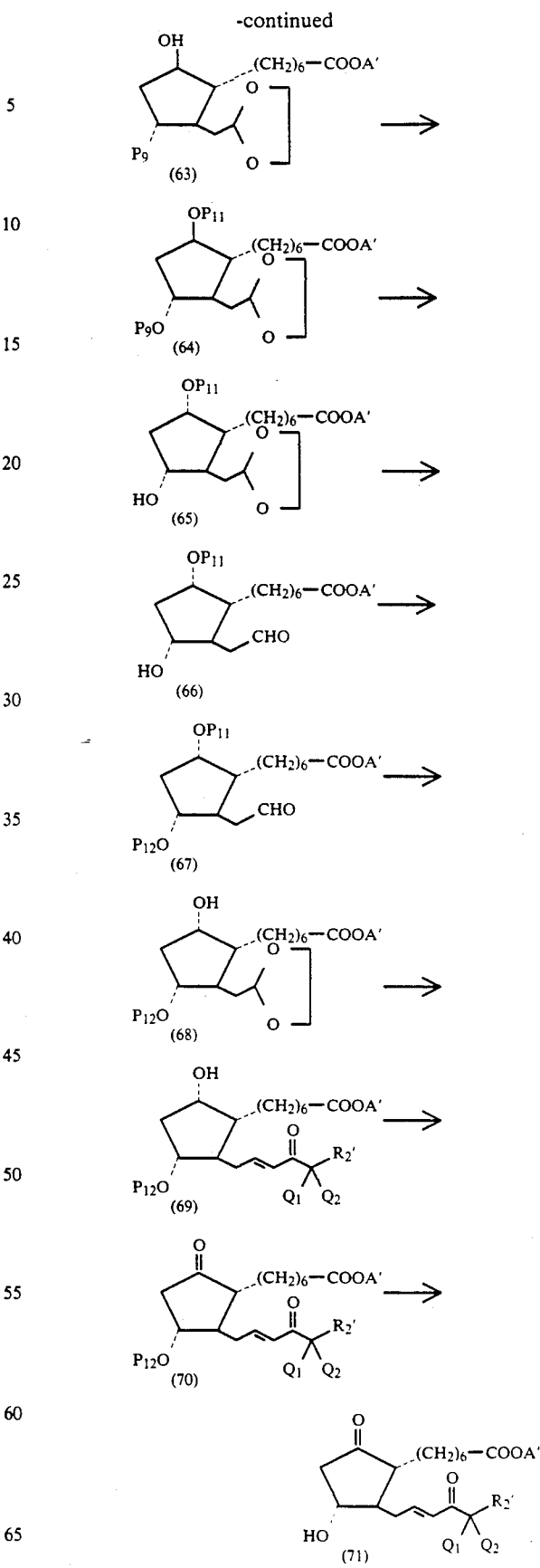

Referring to the above Schemes, the process steps from the compound (1) to the compound (7) show a reaction for elongation of the carbon chain. In the first place, a leaving group (such as tosyl) is introduced to Corey lactone (1) having an appropriate protecting group (for example, 4-phenylbenzoyl) (commercially available) to form the compound (2), which is reacted with a compound generating cyamide ion to give the nitrile (3). Deprotection of it produces the compound (4), the cyano group in which is hydrolyzed to form the compound (5). After introducing a protective group (preferably acyl such as acetyl) to give the compound (6), the carboxy group is reduced to yield the compound (7) that is a compound in which the number of the carbon atoms in the chain is increased by 1.

The compound (7) is oxidized (for example, by Collins oxidation) into the compound (8), which is reacted with (2-oxoalkyl)phosphonate having desired $Q_1$, $Q_2$ and $R_2$ to yield the compound (9). As the phosphonate, (3,3-difluoro-2-oxoalkyl)phosphonate (when $Q_1$ and $Q_2$ are fluorine), (3,3-dimethyl-2-oxoalkyl)phosphonate (when $Q_1$ and $Q_2$ are methyl) or (2-oxo-4-phenylbutyl)-phosphonate (when $R_2'$ is benzyl) may be used. If a 14,15-dihydro compound is desired, the compound (9) is subjected to reduction of the double bond to form the compound (10), and of which oxo group is reduced to give the compound (11), of which hydroxy group is protected to give the compound (12). The acyl protecting group for the hydroxy group at position 11 is removed to give the compound (13) and another protecting group (such as tetrahydropyranyl) is introduced to form the compound (14), of which the lactone ring is then reduced to the corresponding lactol (15). To this is introduced an alpha-chain by Witig reaction to produce the compound (16), which is esterified to the compound (17) and protection group of the hydroxy group at position 16 is removed to give the compound (18). Oxidation of the hydroxy groups at position 16 and 9 giving the compound (19) and deprotection of the hydroxy group at position 11 gives the desired compound (20). In the above preparation, when the reduction of the compound (9) to the compound (10) is omitted, the compound wherein B is —CH$_2$—CH=CH= is obtained. The compound wherein B is —CH=CH—CH$_2$ can be obtained from Corey lactone (1) which is oxidized, without the reaction for elongation of the carbon chain, to give the aldehyde (24), which is reacted with a (3-hydroxyalkyl)triaryl-phosphonium halide (B) to give the compound (25). This compound is processed in a manner similar to that for the preparation of the compound (12) to produce the desired compound. This is a mixture of cis- and trans-compounds in respect of the double bond at positions 13 and 14, and can be separated by suitable conventional means. The compound wherein $R_1'$ is —CH$_2$—CH$_2$— can be obtained by using appropriately selected alpha-chain introducing agent or by reducing the compound (18), followed by oxidation and deprotection, via the dihydro compound (33) and the diketone (34). The compound wherein A' is a hydrogen atom is obtained after hydrolysis of the compound (20).

In another process, the compound (18) is hydrolyzed to the compound (21), which is oxidized with an oxidizing agent, for example chromic acid, to the compound (22) and then the protecting group of the hydroxy group at position 11 is removed to produce the desired compound (23).

In a further process, in which the compound (I) wherein X is other than a hydroxy group (for example, X is lower alkyl) is desired, the lactone ring of the compound (13) is reduced to form the compound (26), to which the alpha-chain is introduced by Witig reaction to give the compound (27). The hydroxy group at position 11 is protected with, for example, a monocyclic arylsulfonyl group to give the compound (28), which is oxidized (by, for example, Jones oxidation) to be the compound (29). This is reacted with a lower alkyl copper complex to

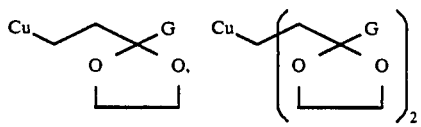

wherein G is alkyl yield the compound (30), of which protection group for the hydroxy group at position 16 is removed. The obtained alcohol (31) is oxidized to produce the desired compound (32).

The PGD-type compounds can be obtained by reducing the compound (13) to the lactol (36), to which the alpha-chain is introduced to form the diol (37). This is converted to the 11-protected compound (38), 9,11-deprotection compound (39), 9-protected compound (40), 16-deprotected compound (41) and then to diketone (42), which at position 9 is removed to produce the compound (43).

The PGA-type compounds can be obtained by oxidation of the 16-deprotected compound (44), which is obtained from the compound (29), to the compound (45).

The PGF-type compounds can be obtained after introduction of a protective group to the compound (27) to give the compound (46), which is deprotected at the side chain to form the compound (47), oxidized to the compound (48) and then deprotected to produce the compound (49). The 6-keto compounds are produced by the reaction with the 5,6-ethylenic compound (50) with N-bromosuccinimide or iodine to form the compound (51), which is treated with DBU (1,8-diazabicyclo-[5.4.0]undec-7-ene). The 5,6-dehydro compounds (i.e. acetylenic compounds) are obtained by 5,6-ethylenic compound (50) with N-bromosuccinimide or iodine to form the compound (51), which is treated with DBU (1,8-diazabicyclo-[5.4.0]undec-7-ene). The 5,6-dehydro compounds (i.e. acetylenic compounds) (54) are obtained by the reaction with the copper enolate, generated from the compound (53) and copper complex, with 6-alkoxycarbonyl-1-iodo-2-hexyne.

Further, 14,15-ethylenic compounds (71) can be prepared from compound (8) via compounds (55)–(70). Thus, the aldehyde functionality of the compound (8) is protected by converting it into acetal using ehtylene glycol to give the compound (55), which is deprotected to produce the alcohol (56). The alcohol (57) is reprotected with another protective group such as tetrahydropyranyl and then reduced to the lactol (58), to which the alpha-chain is introduced by Witig reaction to give the compound (59). The carboxy group is esterified to produce the compound (60) and the hydroxy group is protected by an easily clearable protective group such as silyl to give the compound (61). The unsaturation in the alpha-chain is catalytically hydrogenated to form the compound (62), which is deprotected to give the compound (63) and re-protected by another protective group such as acyl to produce the compound (64). The protected hydroxy at position 3 is deprotected to the compound (65) and then the protected aldehyde is deprotected to the compound (66). The free hydroxy is re-protected to give the compound (67). The protected hydroxy at position 5 is deprotected and aldehyde is protected to produce the compound (68), which is reacted with (2-oxoalkyl)phosphonate having desired $Q_1$, $Q_2$ and $R_2'$ to give the compound (69). This is then oxidized to the compound (70), which is deprotected to the desired compound (71).

Since the compounds (I) have not only improved chemical stability and reduced rate of metabolic degradation but also desired activity or activities out of a wide range of activities of PGs (cf. for example Kirk-Othmer ENCYCLOPEDIA OF CHEMICAL TECHNOLOGY, 3rd. Ed., Supplement Vol., P.721) with less or almost no activity or activities undesirous for human or other animal in the situation is which the compounds are administered, the said compounds are useful as new PG derivatives having selected activity or activities. Such activity or activities can be measured by the conventional pharmacological assay methods which have been used for evaluating the activities of natural and synthetic PGs. In addition, the compounds of the invention are useful as stable reference agents having activities of PGs and usable in comparative biochemical test.

EXAMPLE

The practical embodiments for the production of the invention are illustratively shown in the following the reaction with the copper enolate, generated from the compound (53) and copper complex, with 6-alkoxycarbonyl-1-iodo-2-hexyne.

The 15-dehydroxy-16-oxo-PG compounds used in the present invention have activities useful for preparing a medicament for treatment of allergic diseases, treatment of inflammatory diseases, antihistaminic agent, leukotriene antagonist, platelet activating factor antagonist or branchodilator. Such activities can be measured by the standard methods for each of activities.

The compounds used in the present invention may be used as a medicine for animals and human beings and usually applied systemically or locally by such methods as ophthalmic, nasal or oral administration, oral administration, intravenous injection (including instillation), subcutaneous injection, suppository and the like. While the dosage will vary depending on the particular animal or human patient, age, body weight, symptom to be treated, desired therapeutic effect, administration route, term of treatment and the like, satisfactory effects will be obtained with the dosage of 0.05–100 μg/eye administered locally, or 0.001–500 mg/kg administered systemically in 2 to 4 divided doses a day or as a sustained form.

The ophthalmic composition used according to the invention includes ophthalmic solution, ophthalmic ointment and the like. The ophthalmic solution can be prepared by dissolving an active ingredient in a sterile aqueous solution such as a physiological saline or a buffered solution, or as a combination of a solid and a solution for dissolving said solid to make a ready-to-use preparation. The ophthalmic ointment can be prepared by mixing an active ingredient with an ointment base.

The nasal composition used according to the invention includes nasal solution, nasal spray and the like. The nasal solution can be prepared by dissolving an active ingredient in a sterile aqueous solution such as a physiological saline or a buffered solution, or as a combination of a solid and a solution for dissolving said solid to make a ready-to-use preparation. The nasal spray can be prepared such that an active ingredient can be sprayed in the form of drop of liquid or dust by propellant gas or compressed air.

As a solid composition of this invention for oral administration, tablets, troches, buccals, capsules, pills, powders, granules and the like are included. The solid composition containing one or more active substances is mixed with at least an inactive diluent, e.g. lactose, cellulose, silicic acid anhydride, etc. The composition may contain additives other than the inactive diluent, for example, lubricants, a disintegrator. Tablets and pills may be coated with an enteric or gastroenteric film, if necessary, and furthermore they may be covered with two or more layers. Additionally, the composition may be in the form of capsules made of substance easily absorbed. The composition may be in the form of buccals, when an immediate effect is desired.

Liquid compositions for oral administration include pharmaceutically acceptable emulsions, solutions, suspensions, syrups, elixirs and the like and contain a commonly used inactive diluent e.g. purified water or ethyl alcohol. The composition may contain additives e.g. wetting agents, suspending agents, sweeteners, flavors, perfumes and preservatives.

The composition of the present invention may be in the form of sprays which may contain one or more active ingredients and which can be prepared according to a well known methods.

An injection of this invention for non-oral administration includes sterile aqueous or nonaqueous solutions, suspensions, and emulsions. The composition may contain other additives, e.g. preservatives, wetting agents, emulsifying agents, dispersing agents and the like. These are sterilized by filtration through, e.g. a bacteria-retaining filter, compounding with a sterilizer, gas sterilization or radiation sterilization. These can be prepared by producing a sterilized water or a sterilized solvent for injection before use.

Another formulation according to the present invention is a rectal or vaginal suppository. This can be prepared by mixing at least one active compound according to the invention with a suppository base and optionally containing nonionic surfactant for improving absorption.

A more complete understanding of the present invention can be obtained by reference to the following Preparation Examples, Formulation Examples and Test Examples which are provided herein for purpose of illustration only and are not intended to limit the scope of the invention.

PREPARATION EXAMPLE 1

Preparation of 15-dehydroxy-17,17-difluoro-13,14-dihydro-16-oxo-PGE$_2$ (20) methyl ester [The IUPAC nomenclature:methyl (Z)-7-[(1 R)-(2 R,3 R)-2-(5,5-difluoro-4-oxooctyl)-3-hydroxy-5-oxocyclopentyl]-hept-5-enoate]

1-1) Preparation of (1 S ,5 R,6 R,7 R)-6-cyanomethyl-7-hydroxy-2-oxabicyclo[3.3.0]octan-3-one (4)

P-toluenesulfonyl chloride (30.3 g) was added to a solution of commercially available (−)-Corey lactone (1) (15.0 g) in pyridine, and the resultant mixture was stirred for 15 hours.

The reaction mixture was worked up with the conventional procedure to give the crude tosylate (2).

The tosylate (2) was dissolved in dimethyl sulfoxide and sodium cyanide (3.92 g) was added thereto, and the resultant mixture was stirred at 60° to 70° C. for 2 hours The reaction mixture was worked up with the conventional procedure to give the crude cyano compound (3). The crude cyano compound (3) was dissolved in methanol, and potassium carbonate (2.76 g) was added thereto, and the resultant mixture was stirred for 15 hours. The reaction mixture was concentrated under reduced pressure, and the obtained residue was chromatographed on a silicagel column to give the titled compound (4).

Yield: 3.93 g (51%)

1-2) Preparation of 2-{(6 R)-(1 S ,5 R,7 R)-7-acetoxy-3-oxo-2-oxabicyclo[3.3.0]octyl}-acetic acid (6)

(1 S ,5 R,6 R,7 R)-6-Cyanomethyl-7-hydroxy-2-oxabicyclo[3.3.0]octan-3-one (4) (1.25 g) was dissolved in 1N sodium hydroxyde solution and the resultant mixture was stirred at 100° to 110° C. The reaction mixture was allowed to be cool, neutralized with hydrochloric acid and concentrated under reduced pressure. To the obtained residue were added ethyl acetate and methanol, and insoluble materials were removed by filtration. The filtrate was concentrated under reduced pressure to give the crude carboxylic acid (5). To the carboxylic acid (5) were added acetic anhydride (20 ml) and pyridine (10 ml), and the resultant mixture was stirred for 15 hours. The reaction mixture was concentrated under reduced pressure and the obtained residue was treated with 1N hydrochloric acid and the resultant mixture was stirred for 1 hour. The reaction mixture was worked up with the conventional procedure to give the crude titled compound (6).

1-3) Preparation of (1 S ,5 R,6 R,7 R)-7-acetoxy-6-(2-hydroxy-ethyl)-2-oxabicyclo[3.3.0]octan-3-one (7)

The product obtained in 1-2), namely 2-[(6 R)-(1 S ,5 R,7 R)-7-acetoxy-3-oxo-2-oxabicyclo[3.3.0]octyl]acetic acid (6), was dissolved in ethyl acetate and the resultant solution was cooled to 0° C. Boron dimethyl sulfide complex (0.65 ml) was added and the solution was stirred for 3 hours at room temperature. Methanol (6 ml) was added to the reaction mixture and the resultant mixture was concentrated under reduced pressure. The obtained residue was subjected to silicagel column chromatography to give the titled compound (7).

Yield: 0.803 g (51%, calculated from Compound (4))

1-4) Preparation of (1 S ,5 R,6 R,7 R)-7-acetoxy-6-[(E)-5,5-difluoro-4-oxo-2-octenyl]-2-oxabicyclo[3.3.0]octan-3-one (9)

A solution of oxalyl chloride (0.90 ml) in methylene chloride was cooled to −78° C. and dimethyl sulfoxide (DMSO) (1.64 ml) was added thereto.

To the resultant mixture was added (1 S ,5 R,6 R,7 R)-7-acetoxy-6-(2-hydroxyethyl)-2-oxabicyclo[3.3.-0]octan-3-one (7) (1.77 g) in methylene chloride. After 30 minutes, the resultant solution was warmed to −30° C. Trimethylamine (3.28 ml) was added and the mixture was stirred for additional 30 minutes. To the reaction mixture was added saturated ammonium chloride solution. The resultant mixture was worked up with the conventional procedure to give the crude aldehyde product (8).

To a solution of thallium(I) ethoxide (1.29 g) in tetrahydrofuran (THF) was added a solution of dimethyl (3,3-difluoro-2-oxohexyl)phosphonate (1.39 g) in THF. The resultant solution was cooled to 0° C., followed by addition of a solution of the aldehyde (8) in THF. The resultant mixture was stirred for 15 hours, and neutralized with acetic acid. An aqueous potassium iodide solution was added and insoluble matters were removed by filtration. The filtrate was worked up with the conventional procedure and the obtained residue was subjected to silicagel column chromatography to give the title compound (9).

yield: 0.967 g (54%)

1-5) Preparation of (1 S ,5 R,6 R,7 R)-7-acetoxy-6-{5,5-difluoro-4-(RS)-hydroxyoctyl}-2-oxabicyclo [3.3.0]octan-3-one (11)

Palladium on charcoal (0.200 g) was added to a solution of (1 S,5 R,6 R,7 R)-7-acetoxy-6-[(E)-5,5-difluoro-4-oxo-2-octenyl]-2-oxabicyclo[3.3.0]octan-3-one (9) (1.55 g) in ethyl acetate. The resultant mixture was stirred for 15 hours under a hydrogen atmosphere. The reaction mixture was filtered and the filtrate was concentrated under reduced pressure to give the crude ketone (10).

Sodium borohydride (0.169 g) was added to a solution of crude ketone (10) in methanol. After 30 minutes, acetic acid was added and the resultant mixture was worked up with the conventional procedure. The obtained crude product was subjected to silicagel column chromatography to give the titled compound (11).

Yield: 1.52 g (97%)

1-6) Preparation of (1S,5 R,6 R,7 R)-6-{4(RS)-t-butyl dimethylsiloxy-5,5-difluorooctyl}-7-hydroxy-2-oxabicyclo-[3.3.0]octan-3-one (13)

Imidazol (1.78 g) and t-butyldimethylsilyl chloride (1.97 g) were added to a solution of (1S,5 R,6 R,7 R)-7-acetoxy-6-{5,5-difluoro-4-(RS}-hydroxyoctyl}-2-oxabicyzlo[3.3.0]-octan-3-one (11) (1.52 g) in N,N-dimethyl formamide. The resultant solution was stirred for 3 days.

The reaction mixture was worked up with the conventional procedure to give the crude silyl product (12). The obtained silyl product (12) was dissolved into methanol, followed by addition of potassium carbonate (0.60 g). The resultant mixture was stirred for 2 hours. The reaction mixture was worked up with the conventional procedure and the obtained product was subjected to silicagel column chromatography to give the titled compound (13).

Yield: 1.63 g (89%).

1-7) Preparation of (1S,5 R,6 R,7 R)-6-{4(RS)-t-butyl-dimethylsiloxy-5,5-difluorooctyl}-7-tetrahydropyranyloxy-2-oxabicyclo[3.3.0]octan-3-one (14)

To a solution of (1S,5 R,6 R,7 R)-6-[4(RS)-t-butyl-dimethyl-siloxy-5,5-difluorooctyl]-7-hydroxy-2-oxabicyclo-[3.3.0]octan-3-one (13) (1.63 g) in methylene chloride were added dihydropyran (1.70 ml) and p-toluene sulfonic acid monohydrate (20 mg). After 30 minutes, the resultant mixture was worked up with the conventional procedure and the obtained residue was subjected to silicagel column chromatography to give the titled compound (14).

Yield: 1.93 g (99%).

1-8) Preparation of methyl (Z)-7-[(lR)-(2 R,3 R,5 S)-2-{4(RS)-t-butyldimethylsiloxy-5,5-difluorooctyl}-5-hydroxy-3-tetrahydropyranyloxycyclopentyl]hept-5-enoate (17)

Diisobutylaluminium hydride (DIBAL-H) (1.0M, 11.5 ml) was added to a solution of (1S,5 R,6 R,7 R}-6-{4(RS)-t-butyl-dimethylsiloxy-5,5-difluorooctyl}-7-tetrahydro-pyranyloxy-2-oxabicyclo[3.3.0]octan-3-one (14) (1.93 g) in toluene. After 30 minutes, methanol and a saturated Rochelle salt solution were added and the resultant mixture was worked up with the conventional procedure to give the crude lactol (15).

To a suspension of (4-carboxybutyl)-triphenyl-phosphonium bromide (6.80 g) in THF was added dropwise a solution of potassium t-butoxide (1.0M, 30.7 ml). The resultant mixture was stirred for 15 minutes. The reaction mixture was cooled to −40° C. and a solution of the lactol (15) prepared above in tetrahydrofuran was added thereto. The reaction temperature was kept at 25° C. while stirring for 15 hours and worked up with the conventional procedure to give the crude carboxylic acid (16).

To a solution of the crude carboxylic acid (16) in ether was added a solution of diazomethane in ether prepared with the ordinal method. The reaction mixture was concentrated under reduced pressure, and the obtained residue was subjected to column chromatography with silica gel to give the titled compound (17).

Yield: 1.90 g (82%)

1-9) Preparation of methyl (Z)-7-[(lR)-(2 R,3 R,5 S)-2-{5,5-difluoro-4(R,S)-hydroxyoctyl}-5-hydroxy-3-tetrahydro-pyranyloxycyclopentyl]hept-5-enoate (18)

To a solution of methyl (Z)-7-[(1 R)-(2 R,3 R,5 S)-2-{4 (RS)-t-butyldimethylsiloxy-5,5-difluorooctyl}-5-hydroxy-3-tetrahydropyranyloxycyclopentyl]hept-5-enoate (17) (1.90 g) in tetrahydrofuran was added tetrabutylammonium fluoride in tetrahydrofuran (1.0M, 15.7 ml). The resultant mixture was stirred at room temperature for 3 days. The reaction mixture was concentrated under reduced pressure and the obtained residue was subjected to silicagel column chromatography to give the titled compound (18).

Yield: 1.16 g (75%)

1-10) Preparation of methyl (Z)-7-[(1 R)-(2 R,3 R)-2-(5,5-difluoro-4-oxooctyl)-5-oxo-3-tetrahydropyranyloxy-cyclopentyl]hept-5-enoate (19)

A solution of oxalyl chloride (0.165 ml) in methylene chloride was cooled to −78° C. and dimethyl sulfoxide (DMSO) (0.30 ml) was added thereto.

To the above solution was added a solution of methyl (Z)-7-[(1 R)-(2 R,3 R,5 S)-2-{5,5-difluoro-4(RS)-hydroxy-octyl}-5-hydroxy-3-tetra-hydropyranyloxycyclopentyl]hept- 5-enoate (18) (0.244 g) in methylene chloride. The resultant mixture was warmed to −25° C. and stirred for 1 hour. Triethylamine (0.60 ml) was added thereto and the reaction mixture was stirred for additional 30 minutes, poured into 1N hydrochloric acid, and then worked up with the conventional procedure. The obtained product was subjected to silicagel column chromatography to give the titled compound (19).

Yield: 0.20 g (83%), 1-11) Preparation of 15-dehydroxy-17,17-difluoro-13,14-dihydro-16-oxo-PEG$_2$ methyl ester [methyl (Z)-7-{(1 R)-(2 R,3 R)-2-(5,5-difluoro-4-oxooctyl)-5-oxo-3-hydroxy-cyclopentyl}hept-5-enoate (20)]

Methyl (Z)-7-[(1 R)-(2 R,3 R)-2-{5,5-difluoro-4-oxo-octyl}-5-oxo-3-tetrahydropy:ranyloxycyclopentyl]-hept-5-enoate (19) (0.20 g) was dissolved in a mixed solvent of acetic acid, water and tetrahydrofuran (4:2:1) and the resultant solution was stirred at 45 to 50° C. for 3 hours. The reaction mixture was concentrated under reduced pressure and the obtained product was subjected to silicagel column chromatography and further to medium pressure chromatography on Rober column (Merck & Co.,Inc. ODS, type B) to give the titled compound (20).

Yield: 0.124 g (75%)

Compound (20) ($Q_1=Q_2=F$, $R_2'$=propyl, $A'$=methyl)

$^1$HNMR (CDCl$_3$)δ0.98(t,3H,J=7Hz),1.1-2.80 (m,22H),3.11(m,1H),3.68(s,3H),4.12-4.27(m,0.73H),4.-32-4.47 (m,0.27H),5.25-5.54(m,2H),

MS (DI—EI)m/z402(M+),384(M+—$^H{_2}$O),368(M+—HF—H$_2$O),353(M+-OCH$_3$—H$_2$O),309(M+—$C_4H_7F_2$)

PREPARATION EXAMPLE 2

Preparation of 15-dehydroxy-17,17,-difluoro-13,14-dihydro-16-oxo-PGE$_2$ (23) [The IUPAC nomenclature:(Z)-7-{(1 R)-(2 R,3 R)-2-(5,5-difluoro-4-oxooctyl)-5-oxo-3-hydroxy-cyclopentyl}hept-5-enoic acid]

2-1) Preparation of (Z)-7-{(1 R)-(2 R,3 R)-2-(5,5-difluoro-4-oxooctyl)-5-oxo-3-tetrahydropyranyloxycyclopentyl}hept-5-enoic acid (22)

1N Sodium hydroxide solution (4.8 ml) was added to a solution of methyl (Z)-7-[(1 R)-(2 R,3 R,5 S)-2-{5,5-difluoro-4(RS)-hydroxyoctyl}-5-hydroxy-3-tetrahyropyranyloxy-cyclopentyl]hept-5-enoate (18) (0.457 g) in methanol. The resultant mixture was stirred for 4 hours and treated in the conventional manner to give dialcohol (21).

Chromic acid (3.67 g) was added to pyridine (5.93 ml) in methylene chloride. The resultant mixture was stirred for 1 hour and celite was added thereto. A solution of the diol (21) in methylene chloride was added and the resultant mixture was stirred for 30 minutes. Then, sodium bisulfate (30 g) was added thereto. The reaction mixture was worked up with the conventional procedure to give a crude product, which was subjected to procedure silicagel (Mallincklodt, CC-4) column chromatography to give the titled compound (22).

Yield: 0.231 g (53%)

2-2) Preparation of 15-dehydroxy-17,17-difluoro-13,14-dihydro-16-oxo-PGE$_2$ (23) [The IUP nomenclature: (Z)-7-{(1 R)-(2 R,3 R)-2-(5,5-difluoro-4-oxooctyl)-5-oxo-3-hydroxycyclopentyl}hept-5-enoic acid]

A solution of (Z)-7-[(1 R)-(2 R,3 R)-2-(5,5-difluoro-4-oxooctyl)-5-oxo-3-tetrahydropyranyloxycyclopentyl]-hept5-enoic acid (22) (0.231 g) in a mixed solvent of acetic acid, water and tetrahydrofuran (4:2:1) was stirred at 45° C. for 3.5 hours. The reaction mixture was concentrated under reduced pressure and the obtained residue was subjected to medium pressure chromatography on a Rober column (Merck, & Co., Inc., ODS, type B) to give the titled compound (23).

Yield: 0.110 g (58%)

Compound (23) ($Q_1=Q_2=F$, $R_2'=$propyl) .

$^1$HNMR (CDCl$_3$)δ1.00(t,3H,J=7Hz),1.10-2.80(m,22H),4.12-4.27(m,0.71H),4.32-4.46(m,0.29H),5.27-5.55(m,2H),4.0-6.5 (br.s,2H).

MS (DI-EI)m/z388(M+),370(M+-H$_2$O).

PREPARATION EXAMPLE 3

Preparation of 15-dehydroxy-17,17-difluoro-13,14-dihydro-16-oxo-PGE$_2$ isopropyl ester (20) [The IUPAC nomenclature: Isopropyl (Z)-7-{(1 R)-(2 R,3 R)-2-(5,5-difluoro-4-oxooctyl)-3-hydroxy-5-oxocyclopentyl}hept-5-enoate] 3-1) Preparation of Isopropyl (Z)-7-[(1 R)-(2 R,3 R,5 S)-2-{4(R,S)-t-butyldimethylsiloxy-5,5-difluorooctyl}-5-hydroxy-3-tetrahydropyranyloxycylopentyl]hept-5-enoate (17)

To a solution of the crude carboxylic acid (16) in acetonitrile were added isopropyl iodide (0.85 ml) and 1,8-diazabicyclo[5.4.0]undec-7-ene (DBU) (1.29 ml). The resultant mixture was kept at 60° to 65° C. for 2 hours. The crude product obtained after the usual work-up was subjected to silicagel column chromatography, to give the titled compound (17).

Yield: 1.1g (87%)

3-2]Preparation of isopropyl (Z)-7-[(1 R)-(2 R,3 R,5 S)-2-{4(R,S)-hydroxy-5,5-difluorooctyl}-5-hydroxy-3-tetrahydropyranyloxycylopentyl]hept-5-enoate (18)

To a solution of the compound (17) (1.1g) in THF was added tetrabutylammonium fluoride (1M THF, 5.5 ml). The resultant mixture was stirred for 1 hour and 20 minutes. The product obtained after the usual work-up was subjected to silicagel column chromatography to give the titled compound (18).

Yield: 0.906 g (100%)

3-3) Preparation of isopropyl (Z)-7-{(1 R)-(2 R,3 R,5 S)-2-(5,5-difluoro-4-oxooctycylopentyl}hept-5-enoate (19)

A solution of oxalyl chloride in methylene chloride (2M, 3.5 ml) was cooled to $-78°$ C., followed by addition of DMSO (1.1 ml). A solution of the compound (18) (0.906 g) in methylene chloride (11 ml) was added dropwise. The resultant mixture was stirred at the range of $-35$ to $-25°$ C. for 1.5 hours, and triethylamine (2.1ml) was added dropwise. After 20 minutes, 1Nhydrochloric acid was added. The crude product obtained after the usual work-up was subjected to silicagel column chromatography to give the titled compound (19).

Yield: 0.785 g (87.7%)

3-4) Preparation of isopropyl (Z)-7-{(1 R)-(2 R,3 R)-2-(5,5-difluoro-4-oxooctyl)-5-oxo-3-hydroxycylopentyl}hept-5-enoate (20)

A solution of the compound (19) (0.785 g) in a mixed solvent of acetic aid, THF and water (3:1:1, 70 ml) was kept at 50° C. for 4.5 hours. The crude product obtained after the usual work-up was subjected to silicagel column chromatography to give the titled compound (20).

Yield: 0.335 g

Compound (20) ($Q_1=Q_2=F$, $R_2'=$propyl, $A'=$methyl)

$^1$HNMR (CDCl$_3$)δ0.94(t,3H,J=7.4Hz),1.20(d,6H,J=6.2Hz), 1.3-2.9(m,22H),4.17(m,1H),4.98(hept,1H,J=62Hz),5.22-5.52 (m,2H).

MS (DI-ZI) m/z 430(M$^{30}$)412(M+$-^H{_2}$O),371(-M+$-$C$_3$H$_7$O), 353(M+$-$C$_3$H$_7$O$-$H$_2$O).

PREPARATION EXAMPLE 4

Preparation of 11,15-didehydroxy-17,17-difluoro-13,14-dihydro-11-methyl-16-oxo-PGE$_2$ methyl ester (32) [The IUPAC nomenclature: methyl (Z)-7-{ (1 R,2 S,3 R)-2-(5,5-difluoro-4-oxooctyl)-3-methyl-5-oxocyclopentyl}hept-5-enoate]

4-1) Preparation of {1S,3(R,S),5 R,6 R,7 R}-6-{4(R,S)-t-butyldimethylsiloxyoctyl-5,5-difluorooctyl}-3,7-dihydroxy-2-oxabicyclo[3.3.0]octane (26)

A solution of (1S, 5 R, 6 R, 7 R)-6-{4(R,S)-t-butyldimethylsiloxy-5,5-difluorooctyl}-7-hydroxy-2-oxabicyclo-[3.3.0]octane-3-one (13) (1.06 g) in toluene was cooled to $-78°$ C. and DIBAL-H (1.5M, 7.56 ml) was added dropwise thereto. After 30 minutes methanol (8 ml) was added. The reaction mixture was worked up with the conventional manner to give the lactol (26).

4-2) Preparation of methyl (Z)-7[(1 R)-(2 R, 3 R, 5S)-2}(4(R,S)-t-butyldimethylsiloxy-5,5-difluorooctyl}-3,5-dihydroxycylopentyl]hept-5-enoate (27)

To a suspension of (4-carboxybutyl)triphenyl-phosphonium bromide (6.7 g) in THF (5 ml) was added dropwise potassium t-butoxide (1.0 M, in THF solution) (30.2 ml). The resultant mixture was stirred at room temperature for 30 minutes, and then cooled to $-40°$ C. A solution of lactol (26) in THF (15 ml) was added thereto. The resultant mixture was stirred overnight at $-20°$ C. The crude carboxylic acid obtained after the usual work-up was esterified with diazomethane. The obtained product was subject to silicagel column chromatography to give the idol (27).

Yield: 1.12 g (85%)

4-3) Preparation of methyl (Z)-7-[(1 R)-(2 R,3 R,5S)-2-{(4(R,S)-t-butyldimethylsiloxy-5,5-difluorooctyl}-5-hydroxy-3-(p-toluenesulfoxy)cylopentyl]hept-5-enoate (28)

A solution of the diol (27) (0.574 g) in pyridine was cooled to $-20°$ C., followed by addition of p-toluenesulfonyl chloride (2.1 g). The resultant mixture was stirred for 1 hour at $-20°$ C. and for additional 2 hours at 0° C. The crude product obtained after the usual work-up was subjected to silicagel column chromatography to give the monotosylate (28).

Yield: 0.465 g (63%)

4- 4) Preparation of methyl (Z)-7-[(1 R,2 R)-2-{4(R,S)-t-butyldimethylsiloxy-5,5-difluorooctyl}-5-oxocyclopent-3-enyl]hept-5-enoate (31)

A solution of the monotosylate (15) (0.465 g) in acetone (20 ml) was cooled to $-30°$ C. and Jones reagent (0.9 ml) was added dropwise thereto. The resultant mixture was stirred at the range of $-20°$ to 10° C. for 50 minutes, followed by addition of isopropanol (0.9 ml). After stirring for 20 minutes, the reaction mixture was worked up with the conventional procedure. The obtained crude product was subjected to silicagel column chromatography to give the α, β-unsaturated ketone (29).

Yield: 0.201 g (71%)

4-5) Preparation of methyl (Z)-7-[(1 R,2S,3 R)-2{4(R,S)-t-butyldimethylsiloxy-5,5-difluorooctyl}-3-methyl-5-oxocyclopentyl]hept-5-enoate (30)

Copper (II) iodide (0.313 g) was added to anhydrous ether (15 ml). The resultant suspension was cooled to 20° C. and methyl lithium (1.4 M, 2.35 ml) was added thereto. After the resultant mixture became colorless and clear, a solution of the α, β-unsaturated ketone (29) in ether (15 ml) was added thereto. The crude product obtained after the usual work-up was subjected to silicagel column chromatography to give the titled compound (30).

Yield: 0.201 g (71%)

4-6) Preparation of methyl (Z)-7-[(1 R, 2S, 3 R)-2{4(R,S)-hydroxy-5,5-difluorooctyl}-3-methyl-5-oxocyclopentyl]-hept-5-enoate (31)

Hydrofluoric acid (1 ml) was added to a solution of the compound (30) (0.201 g) in acetonitrile (20 ml). The resultant mixture was stirred at room temperature for 1 hour. The crude product obtained after the usual work-up was subjected to silicagel column chromatography to give the alcohol (31).

Yield: 0.138 g (88%)

4-7) Preparation of methyl (Z)-7-[(1 R, 2S, 3 R)-2-(5,5-difluoro-4-oxooctyl)-3-methyl-5-oxocyclopentyl]hept-5-enoate (32)

Celite (5 g) was added to Collins reagent prepared from chromic anhydride (1.2 g) and pyridine in methylene chloride (20 ml), followed by addition of a solution of the alcohol (31) (0.138 g) in methylene chloride (10 ml). The resultant mixture was stirred at room temperature for 30 minutes, followed by the usual work-up. The obtained crude product was subjected to silicagel column chromatography to give the titled compound (32).

Yield: 81%

Compound (32) (X'=methyl, $Q_1=Q_2=F$, $R_2'$=propyl, A'=methyl)

$^1$HNMR (CDCl$_3$)δ0.97(t,3H,J=7.5Hz), 1.13(d,3H,J=6Hz), 1.35-2.80(m,23 H), 3.67(s,3 H), 5.23-5.50(m,2 H).

MS (DI-ZI) m/z 400(M+),369(M+−CH$_3$O)

PREPARATION EXAMPLE 5

Preparation of 15-dehydroxy-17,17-difluoro-13,14-dihydro-16-oxo-PGE$_1$ methyl ester (32) [The IUPAC nomenclature: methyl 7-[(1 R)-(2 R,3S,5S)-2-{5,5-difluoro-4(R,S)-hydroxyoctyl}-5-hydroxy-3-tetrahydropyranyloxycylopentyl]heptanoate (33)

Palladium on carbon (Pd-C) (100 mg) was added to a solution of the diol (18) (0.465 g) in ethyl acetate (30 ml). The resultant mixture was stirred overnight under a hydrogen atmosphere. The reaction mixture was filtered and the filtrate was concentrated under reduced pressure to give the dihydro compound (33).

Yield: 0.450 g (98%)

5-2) Preparation of methyl 7-{(1 R)-(2 R,3 R)-2-(5,5-difluoro-4oxooctyl)-5-oxo-3-tetrahydropyranyloxycylopentyl}heptanoate (34)

Celite (10g) was added to Collins reagent prepared from chromic anhydride (3.67 g) in methylene chloride (20 ml), followed by addition of the dihydro compound (33) (0.450 g) to be oxidized. The crude product obtained after the usual work-up was subjected to silicagel column chromatography to give the diketone (34).

Yield: 0.371 g (83%)

5-3) Preparation of methyl 7-{(1 R)-(2 R, 3 R)-2-(5,5-difluoro-4-oxooctyl)-3-hydroxy-5-oxocyclopentyl}heptanoate (35)

The diketone (34) (0.371 g) was dissolved in a mixed solvent of acetic acid, THF and water (1:3:1, 35 ml), and the resultant solution was stirred overnight. The crude product obtained after the usual work-up was chromatographed on a Rober column (ODS) to give the titled compound (35).

Compound (35) ($Q_1=Q_2=F$, $R_2'$=propyl, A'=methyl)

$^1$HNMR (CDCl$_3$)δ0.98(t,3 H, J=7.5 Hz),1.11-2.9(m,26 H), 3.67(s,3 H),4.114 4.25(m,1 H)., MS (DI-ZI) m/z 404(M+),386(M+−H$_2$O),355(-M+−H$_2$O−CH$_3$O)

EXAMPLE 6

Preparation of 15-dehydroxy-17,17-difluoro-13,14-dihydro-16-oxo-PGD$_2$ methyl ester (43) [The IUPAC nomenclature: methyl (Z)-7-{(1 R)-(2 R, 5 S)-2-(5,5-difluoro-4-oxooctyl)-5-hydroxy-3-oxocyclopentyl}hept-5-enoate]

6-1) Preparation of methyl (Z)-7-[(1 R)-(2 R,3 R, 5 S)-dihydroxycylopentyl]heptanoate (37)

The lactone (13) (1.06 g) in toluene cooled to −78° C. was reducted with DIBAL-H (1.5 M in toluene, 7.56 ml). The reaction mixture was worked up with the conventional procedure to give the lactol (36). Pottasium butoxide (1.0 M in THF, 30.2 ml) was added to a suspension of (4-carboxybutyl)triphenylphosphonium bromide (6.7 g) in THF and the resultant mixture was stirred at room temperature for 30 minutes, and then cooled to −40° C. A solution of the lactol (36) in THF (15 ml) was added thereto, and the mixture was stirred overnight at −20° C. The crude carboxylic acid obtained after the usual work up was esterified with diazomethane and the reaction mixture was subjected to silicagel column chromatography to give the diol (37).

Yield: 1.12 g (85%)

6-2) Preparation of methyl (Z)-7-[(1 R)-(2 R, 3 R, 5 S)-2-{(R,S)-t-butyldimethylsiloxy-5,5-difluorooctyl}-3-benzoyloxy-5-hydroxycyclopentyl]hept-5-enoate (38)

A solution of the diol (37) (0.564g) and pyridine (8.85ml) in methylene chloride was cooled to −30° C. Benzoyl chloride (0.147 g) was added thereto and the mixture was stirred for 1 hour. An additional amount (0.440 g) of benzoyl chloride was added to the reaction mixture and the mixture was stirred at −20° for 2 hours. The crude produce obtained after the the usual work-up was subjected to silicagel chromatography to give the compound (38).

Yield: 0.567 g (77%)

6-3) Preparation of methyl (Z)-7-[(1 R)-(2 R, 3 R, 5 S)-2-{4(R,S)-t-butyldimethylsiloxy-5,5-difluorooctyl}-3-benzoyloxy-5-tetrahydropyranyloxycylopentyl]hept-5-enoate (39

Dyhydropyran (0.6 ml) was added to a solution of monobenzoate compound (38) (0.567 g) in methylene chloride and the resultant mixture was cooled to 0° C. A catalytic amount of p-toluenesulfonic acid was added thereto and the mixture was stirred for 30 minutes. The crude product obtained after the usual work-up was subjected to silicagel column chromatography to give the titled compound (39).

Yield: 0.689 g 6-4) Preparation of methyl (Z)-7-[(1 R)-(2 R, 3 R, 5 S)-2-{4(R,S)-t-butyldimethylsiloxy-5,5-difluorooctyl}-3-hydroxy-5-tetrahydropyranyloxycylopentyl]hept-5-enoate (40)

Potassium carbonate (0.125 g) was added to a solution of the compound (39) (0.689 g) in methanol, and the resultant mixture was stirred at room temperature for 2 hours. An additional amount (1.75 g) of potassium carbonate was added thereto, and the mixture was left on standing overnight. The crude product obtained after the usual work-up was subjected to silicagel column chromatography to give the monalcohol (40).

Yield: 0.479 g (87%, started from the compound (38))

6-5) Preparation of methyl (Z)-7-[(1 R)-(2 R, 3 R, 5 S)-2-{4(R,S)-hydroxy-5,5-difluorooctyl}-3-hydroxy-5-tetrahydropyranyloxycylopentyl]hept-5-enoate (41)

Tetrabutylammonium fluoride (1.0 M in THF, 3.95 ml) was added to a solution of the monoalcohol (40) (0.479 g) in THF and the mixture was stirred overnight at room temperature. The crude product obtained after the usual work-up was subjected to silicagel column chromatography to give the diol (41).

Yield: 72%

6-6) Preparation of methyl (Z)-7-{(1 R)-(2 R, 5 S)-2-(5,5-difluoro-4oxooctyl)-3-oxo-5-tetrahydropyranyloxycylopentyl}hept-5-enoate (42)

A solution of oxalyl chloride (0.24 ml) in methylene chloride was cooled to −78° C., followed by addition of DMSO (0.44 ml). After 15 minutes, a solution of the diol (41) (0.358 g) in methylene chloride was added dropwise to the resultant mixture. After 30 minutes, the mixture was warmed to −50° C., followed by stirring for 1.5 hours. Then, the reaction mixture was allowed to warm to −35° C. and triethylamine (0.88 ml) was added thereto. The crude product obtained after the usual work-up was subjected to silicagel column chromatography to give the diketone (42).

Yield: 0.188 g (53%)

6-7) Preparation of methyl (Z)-7{(1 R)-(2 R, 5 S)-2-(5,5-difluoro-4oxooctyl)-5-hydroxy-3-oxocyclopentyl}hept-5-enoate (43)

The diketone (42) (0.188 g) was dissolved in a mixed solvent of acetic acid, THF and water (3:1:1, 25 ml) and the resultant mixture was kept at 40° C. for 3.5 hours. The crude product obtained after the usual work-up was subjected to silicagel column chromatography to give the titled compound (43).

Yield: 0.112 g (72%)

Compound (43) ($Q_1=Q_2=F$, $R_2'$=propyl, $A'$=-methyl)

$^1$HNMR (CDCl$_3$)δ0.98(t,3H,J = 7.5 Hz), 1.4–2.8(m,22 H), 3.69(s,3 H),4.1–4.5(m,1 H),5.4–5.6(m,2 H).

MS (DI—ZI) m/z 402(M+),384(M+—H$_2$O),353(-M+—H$_2$O—CH$_3$O) 333(M+—H$_2$O—CH$_3$O—HF)

PREPARATION EXAMPLE 7

Preparation of 15-dehydroxy-17,17-difluoro-13,14-dihydro-16-oxo-PGA$_2$ methyl ester (45) [The IUPAC nomenclature: methyl (Z)-7-{(1 R, 2 R)-2-(5,5-difluoro-4-oxooctyl)-5-oxocyclopent-5enyl} hept-5-enoate]

7-1) Preparation of methyl (Z)-7-[(1 R, 2 R)-2-{5,5-difluoro-4-(R,S)-hydroxyoctyl}-5-oxocyclopentyl-3-enyl]hept-5-enoate (44)

The α,β-unsaturated ketone (29) (0.276 g) was dissolved in a solution of aqueous hydrogen fluoride in acetonitrile (46% aqueous hydrogen fluoride:acetonitrile=95:5) (20 ml), and the resultant mixture was stirred at room temperature for 2 hours. The crude product obtained after the usual work-up was subjected to silicagel column chromatography to give the alcohol (44).

Yield: 0.180 g 7-2) Preparation of methyl (Z)-7-[(1 R, 2 R)-2-{5,5-difluoro-4-oxooctyl}-5-oxocyclopent-3-enyl]-hept-5-enoate (45)

Oxalyl chloride (2 M in CH$_2$Cl$_2$) (0.47 ml) was dissolved in methylene chloride (12 ml), followed by addition of DMSO (0.12 ml). The resultant mixture was cooled to −78° C. for 1 hour. Then, triethylamine (0.23 ml) was added thereto, and the resultant mixture was stirred at −30° C. for 30 minutes.

The crude product obtained after the usual work-up was subjected to silicagel column chromatography to give the titled compound (45).

Yield: 0.126 g (71%)

Compound (45) ($Q_1=Q_2=F$, $R_2'$=propyl, $A'$=-methyl)

$^1$HNMR (CDCl$_3$)δ1.00(t,3H,J = 7.5Hz),1.40—2.80(m,20 H), 3.70(s,3 H), 5.28–5.55(m,2 H),6.17(dd,1 H,J=7.5,J=2.5),7.63(dd, 1 H,J=7.5,J=2.5).

MS (DI-ZI) m/z 384(M+),353(M+—CH$_3$O)

PREPARATION EXAMPLE 8

Preparation of 15-dehydroxy-17,17-difluoro-13,14-dihydro-16-oxo-PGF$_2$α methyl ester (49) [The IUPAC nomenclature: methyl (Z)-7-{(1 R)-(2 R, 3 R, 5 S)-2-(5,5-difluoro-4-oxooctyl)-3,5-dihydroxycylopentyl}hept-5-enoate]

8-1) Preparation of methyl (Z)-7-[(1 R)-(2 r, 3 R, 5 S)-2-{4(R,S)-t-butyldimethylsiloxy-5,5-difluorooctyl}-3,5-ditetrahydropyranyloxy)cylopentyl]hept-5-enoate (46)

A solution of methyl (Z)-7-[(1 R)-(2 R, 3 R, 5 S)-2-{4(R,S)-t-butyldimethylsiloxy-5,5-difluorooctyl}-3,5-dihydroxy-cylopentyl]-hept-5-enoate (27) (0.647 g) in dichloromethane (10 ml) and a catalytic amount of p-toluenesulfonic acid. The reaction mixture was gradually warmed to room temperature and kept for 16 hours at the same temperature. The crude product obtained after the usual work-up was subjected to silicagel column chromatography to give the titled compound (46).

Yield: 0.893 g (100%)

8-2) Preparation of methyl (Z)-7-[(1 R)-(2 R,3 R,5 S)-2-{5,5-difluoro-4(R,S)-hydroxyoctyl}-3,5-di(tetrahydro-pyranyloxy)cyclopentyl]hept-5-enoate (47)

Tetrabutylammonium fluoride (1 M in THF, 3.72 ml) was added to a solution of the compound (46) (0.89 g) in THF (12 ml) and the resultant mixture was stirred for 1 hour. The crude product obtained after the usual work-up was subjected to silicagel column chromatography to give the titled compound.

Yield: 0.676 g (95%)

8-3) Preparation of methyl (Z)-7-[(1 R)-(2 R,3 R,5 S)-2-{5,5-difluoro-4-oxooctyl}-3,5-di(tetrahydropyranyloxy)-cylopentyl]hept-5-enoate (48)

The compound (47) (0.43 ml) was oxidized by Swarn oxidation using 2M oxalyl chloride (0.76 ml), DMSO (0.22 ml) and triethylamine (0.43 ml) in dichloromethane (9 ml). The crude product obtained after the usual work-up was subjected to silicagel column chromatography to give the titled compound (48).

Yield: 0.558 g (82%)

8-4) Preparation of methyl (Z)-7-[(1 R)-(2 R,3 R,5 S)-2-{5,5-difluoro-4-oxooctyl}-3,5-di(tetrahydropyranyloxy)-cylopentyl]hept-5-enoate (49)

The compound (48) (0.558 g) was dissolved in a mixed solvent of acetic acid, water and THF (4:2:1, 49 ml), and the resultant solution was kept at 45° to 50° C. for 2.5 hours. The crude product obtained after the usual work-up was chromatographed on a silicagel column to give the titled compound (49).

Yield: 0.367 g (94%)

Compound (49) ($Q_1=Q_2=F$, $R_2'=$propyl, $A'=$methyl)

$^1$HNMR (CDCl$_3$)δ0.95(t,3 H),1.1–3.0(m,24 H),3.66(s,3 H), 3.95(s,1 H),4.14(s,1 H),5.28–5.52(m,2 H).

MS (DI-ZI) m/z 404(M$^+$),386(H$^+$—H$_2$ I.O),368(-H$^+$—2H$_2$O)

PREPARATION EXAMPLE 9

Preparation of 15-dehydroxy-17,17-difluoro-13,14-dihydro-20-methyl-16-oxo-PGE$_2$ methyl ester (20) [The IUPAC nomenclature: methyl (Z)-7-{(1 R)-(2 R,3 R)-2-(5,5-difluoro-4-oxononyl)-5-oxo-3-hydroxycylopentyl}hept-5-enoate]

The titled compound (20) was prepared from the compound (8) and dimethyl (3,3-difluoro-2-oxoheptyl)phosphonate according to the procedure described for the preparation of 15-dehydroxy-17,17-difluoro-13,14-dihydro-20-methyl-16-oxo-PGE$_2$ methyl ester.

Compound (20) ($Q_1=Q_2=F$, $R_2'=$butyl, $A'=$methyl)

$^1$ HNMR (CDCl$_3$) δ 0.94(t,3 H),1.1–2.9(m,27 H), 3.68(s,3 H),4.2(br.s, 1/2 H),4.4(q, 1/2 H),5.4(m,2 H).

MS (DI-ZI) m/z 384(M$^+$—H$_2$O), 353(M$^+$—H$_2$O—CH$_3$O).

PREPARATION EXAMPLE 10

Preparation of 15-dehydroxy-17,17-difluoro-13,14-dihydro-16-oxo-PGE$_1$ isopropyl ester (35) [The IUPAC nomenclature: isopropyl 7-{(1 R)-(2 R,3 R)-2-(5,5-difluoro-4-oxooctyl)-3-hydroxy-5-oxocyclopentyl}hept-5-enoate]

A solution of 15-dehydroxy-17,17-difluoro-13,14-dihydro-16-oxo-PGE$_2$ isopropyl ester (20) (0.303 g) obtained in Example 3 in ethyl acetate (20 ml) was subjected to hydrogenation with a catalytic amount of 5% Pd-C and hydrogen gas. The reaction mixture was filtered and the filtrate was concentrated to give the crude product, which was chromatographed on a Rober column to give the titled compound (35).

Yield: 0.223 g (73%)

Compound (35) ($Q_1=Q_2=F$, $R_2'=$propyl, $A'=$isopropyl)

$^1$HNMR (CDCl$_3$)δ0.98(t,3 H,J=7.5 Hz),1.21(d,6 H,J=5.5 Hz), 1.24–2.82(m,27 H),4.1–4.5(m,1 H),4.99(Hept,1 H,J=7.5 Hz).

PREPARATION EXAMPLE 11

Preparation of 15-dehydroxy-17,17-difluoro-13,14-dihydro-16-oxo-PGE$_2$ benzyl ester (20) [The IUPAC nomenclature: benzyl (Z)-7-{(1 R)-(2 R,3 R)-2-(5,5-difluoro-4-oxooctyl)-3-hydroxy-5-oxocyclopentyl}hept-5-enoate]

The titled compound (20) was prepared as described in Example 3 except that the crude carboxylic acid (16) in acetonitrile was converted to benzyl ester using benzyl bromide and DBU.

Compound (20) ($Q_1=Q_2=F$, $R_2'=$benzyl)

$^1$HNMR (CDCl$_3$) δ 0.96(d,t,3 H,J=7.5 Hz,J=7.5 Hz), 1.1–2.8(m,23 H),4.18(m,0.7 H),4.36(m,0.3 H),5.11(s,2 H), 5.38(m,2 H),7.35(s,5 H).

PREPARATION EXAMPLE 12

Preparation of 15-dehydroxy-17,17-difluoro-13,14-dihydro-16-oxo-PGE$_1$ [The IUPAC nomenclature: 7-{(1 R)-(2 R,3 R)-2-(5,5-difluoro-4-oxooctyl)-3-hydroxy-5-oxocyclopentyl}heptanoic acid]

The benzyl ester (20) (0.580 g) obtained in Example 11 was subjected to catalytic hydrogenation in ethanol (20 ml) using 5% Pd-C (a catalytic amount) and hydrogen gas. The obtained crude product was purified with HPLC (OD column) to give the titled compound.

Yield: 0.426 g (90%)

$^1$ HNMR (CDCl$_3$) δ 0.98(t,3 H,7.5 Hz],1.1–2.82(m,28 H), 4.07–4.45(m,1 H).

The compound wherein $R_1'$ is —CO—CH$_2$— or $R_1'$ is —C=C— can be prepared as follows.

PREPARATION EXAMPLE 13

Preparation of 15-dehydroxy-13,14-dihydro-6,16-dioxo-PGF$_1α$ isopropyl ester (52)

To a solution of 15-dehydroxy-13,14-dihydro-16,16-ethylenedioxy-11-tetrahydropyranyloxy-PGF$_2α$(50) in a mixed solvent of tetrahydrofuran and methylene chloride was added N-bromosuccinimide equimolar to the compound (50). The resultant mixture was stirred for 5 minutes. The crude product obtained after the usual work-up was chromatographed on a silicagel column to give the compound (51) ($Q_1=Q_2=H$, $R_2'=$propyl, $P_4=$tetrahydropyranyl, $P_7=$ethylene, $A'=$isopropyl). DBU was added to a solution of the compound (50) in toluene, and the resultant mixture was stirred overnight at 40° C. After cooling with ice, the reaction mixture was acidified with 1Nhydrochloric acid. After stirring for 10 minutes, the solution was extracted with ethyl acetate. The crude product obtained after the usual work-up was chromatographed on a silicagel column to give the titled compound (52) (the symbols have the same meanings as above).

PREPARATION EXAMPLE 14

Preparation of 15-dehydroxy-5,6-dehydro-13,14-dihydro-16-oxo-PGE$_2$ methyl ester t-Butyllithium was added dropwise over 30 minutes to a solution of 4,4-ethylenedioxyoctane iodide in ether at −78° C., and the resultant mixture was stirred for 3 hours. A solution of copper(I) iodide and tributylphosphine in ether, previously cooled at -78° C., was added in one portion. The reaction mixture was stirred for 20 minutes to produce a complex (a). Further, a solution of 4 R-t-butyldimethyl-silyloxy-2-cyclopenten-1-one (53) in tetrahydrofuran was added dropwise thereto over 95 minutes, and stirring was continued for 15 minutes. The resultant mixture was transferred in a cooling bath at −30° C. A solution of 8-methoxycarbonyl−2-hexynyl−1-iodide (b) in HMPA was added thereto, and the resultant mixture was stirred at same temperature for 4.5 hours, followed by stirring for additional 12 hours at room temperature. The reaction mixture was poured into saturated aqueous ammonium chloride solution and the organic phase was separated. The crude product obtained after the usual work-up was chromatographed to give the compound (54) ($Q_1=Q_2=H$, $R_2'$=propyl, $P_6$=t-butyldimethylsilyl, $P_7$=ethylene, $A'$=isopropyl), which was deblocked in the usual work-up to give the titled compound.

PREPARATION EXAMPLE 15

Preparation of 15-dehydroxy−17,17-difluoro-13,14-dihydro- 14,15-dehydro-16-oxo-PGE1 methyl ester (71)

15-1) Preparation of (1S,5 R,6 R,7 R)- 7-acetoxy-6-(2,2-ethylenedioxyethyl)-2-oxabicyclo[3.3.0]octan-3-one (55)

The aldehyde (8) (5.527 g) obtained in the usual manner was converted to the corresponding acetal using ethylene glycol (100 ml) and a catalytic amount of p-toluenesulfonic acid in toluene (100 ml). The crude product obtained after the usual work-up was chromatographed on a column of silica gel (hexane/ethyl acetate =1/2) to give the acetal (55).
Yield: 4.300 g (65.1 %).

15- 2) Preparation of (1S,5 R,6 R,7 R)-6-(2,2-ethylenedioxyethyl)-7-hydroxy-2-oxabicyclo[3.3.0]octan-3-one (56)

The acetal (55) (4.180 g) was treated with potassium carbonate (1.18 g) in methanol (100 ml) at room temperature for 2 hours with stirring. The reaction mixture was neutralized with addition of acetic acid, followed by the usual work up to give a crude product. The crude product was chromatographed on a column of silica gel to give the alcohol (56).
Yield: 3.450 g (97.7 %).

15-3) Preparation of (1S,5 R,6 R,7 R)-6-(2,2-ethylenedioxyethyl)-7-tetrahydropyranyloxy-2-oxabicyclo[3.3.0]octan-3-one (57)

The alcohol (56) (3.450 g) was converted to the corresponding tetrahydropyranyl ether with dihydropyran (6.9 ml) and a catalitic amount of p-toluenesulfonic acid in dichloromethane (100 ml). The crude product obtained after the usual work-up was chromatographed on a column of silica gel (hexane/ethyl acetate=1/2) to give the tetrahydropyranyl ether (57).
Yield: 4.701 g (99.6 %).

15-4) Preparation of (1S,(3 RS),5 R,6 R,7 R)-6-(2,2-ethylenedioxyethyl)-7-tetrahydropyranyloxy-2-oxabicyclo[3.3.0]octan-3-ol (58)

The ether (57) (4.700 g) was reduced in toluene (80 ml) at −78° C. with diisobutylaluminum hydride (1.5-M, 12 ml) to give the lactol (58).

15-5) Preparation of Z-7-[(1 R,2 R,3 R,5 S)-2-(2,2-ethylenedioxyethyl)-5-hydroxy-3-(tetrahydropyranyloxy)cyclopentyl]hept-5-enoic acid (59)

(4-Carboxybutyl)triphenylphosphonium bromide (22.03 g) and potassium t-butoxide (1-M, 99.4 ml) were treated in THF (100 ml) to give a ylide, to which was added the previously obtained lactol (58) at 0° C., and the mixture was kept at room temperature overnight. The reaction was worked up in the usual manner to give the carboxylic acid 15-6) Preparation of methyl Z-7-[(1 R,2 R,3 R,5 S)-2-(2,2-ethylenedioxyethyl)-5-hydroxy-3-(tetrahydropyranyloxy)cyclopentyl]hept-5-enoate (60)

The carboxylic acid (59) was treated with diazomethane in ether (150 ml) to give the methyl ester (60). The crude product obtained after the work-up was chromatographed on a column of silica gel (hexane/ethyl acetate =3/2).
Yield: 4.990 g (80.4 %; overall for 2 steps).

15-7) Preparation of methyl Z-7-[(1 R,2 R,3 R,5 S)-5-t-butyldimethylsiloxy-2-(2,2-ethylenedioxyethyl)-3-(tetrahydropyranyloxy)cyclopentyl]hept-5-enoate (61)

The methyl ester (60) (4.990 g) was converted to the corresponding t-butyldimethylsilyl ether (61). The crude product obtained after the usual work-up was chromatographed on a column of silica gel (hexane/ethyl acetate =2/1).
Yield: 6.320 g (99.2 %).

15-8) Preparation of methyl 7-[(1 R,2 R,3 R,5 S)-5-t-butyldimethylsiloxy-2-(2,2-ethylenedioxyethyl)-3-(tetrahydropyranyloxy)cyclopentyl]heptanoate (62)

The t-butyldimethylsilyl ester (61) (1.522 g) was hydrogenated with a catalytic amount of 5 % palladium on carbon in ethyl acetate (20 ml) and hydrogen gas to give the dihydro compound (62).
Yield: 1.457 g (95.4 %).

15-9) Preparation of methyl 7-[(1 R,2 R,3 R,5 S)-2-(2,2-ethylenedioxyethyl)-5-hydroxy-3-(tetrahydropyranyloxy)cyclopentyl]heptanoate (63)

The dihydro compound (62) (1.400 g) was converted to the alcohol (63) with tetrabutylammonium fluoride (1M, 10 ml) in THF (20 ml).
Yield: 0.7725 g (70.4 %).

15-10) Preparation of methyl 7-[(1 R, 2 R, 3 R, 5 S)-5-acetoxy-2-(2,2-ethylenedioxyethyl)-3-(tetrahydropyranyloxy)cyclopentyl]heptanoate (64)

The alcohol (63) (0.7725 g) was converted to the corresponding acetate (64) with 4-dimethylaminopyridine and acetic andyride in dichloromethane (10ml). The crude product obtained after the work-up was chromatographed on a column of silica gel (hexane/ethyl acetate = 3/2)
Yield: 0.8484 g (99.7%).

15-11) Preparation of methyl 7[(1 R, 2 R, 3 R, 5 S)-5-acetoxy-2-(2,2-ethylenedioxyethyl)-3-(hydroxy)-cyclopentyl]heptanoate (65)

The acetate (64) (0.8400 g) was dissolved in a mixed solvent of acetic acid, THF and water (3/1/1, 20 ml), and the solution was kept 50° C. for 3 hours. The crude product obtained after the work-up was chromatographed on a column of silica gel (hexane/ethyl acetate = 1/1).

Yield: 0.3927 g (55.8 %).

15-12) Preparation of methyl 7-[(1 R, 2 R, 3 R, 5 S)-5-acetoxy-2-(2-formylmethyl)-5-(hydroxy)cyclopentyl]heptanoate (66)

The alcohol (65) (0.3725 g) was kept in a mixed solvent of acetic acid, THF and water (3/1/1, 10 ml) at 70° C. for 5 hours. The crude product obtained after the work-up was chromatographed on a column of silica gel (hexane/ethyl acetate = 3/1).

Yield: 0.3284 g (100%).

15-13) Preparation of methyl 7-[(1 R, 2 R, 3 R, 5 S)-5-acetoxy-2-(2-formylmethyl)-5-(tetrahydropyranyloxy)cyclopentyl]heptanoate (67)

The aldehyde (66) (0.3280 g) was converted to the tetrahydropyranyl ether (67) with dihydropyran (0.5 ml) and a catalytic amount of p-toluene-sulfonic acid in dichloromethane (10 ml).

Yield: 0.3772 g (91.5%)

15-14) Preparation of methyl 7-[(1 R, 2 R, 3 R, 5 S)-2-(2-formylmethyl)-5-hydroxy-3-(tetrahydropyranyloxy)cyclopentyl]heptanoate (68)

The acetate (67) (0.3772 g) was converted to the corresponding alcohol (68) with potassium carbonate (0.083 g) in methane (10 ml). The crude product obtained after the work-up was chromatographed on a column of silica gel (hexane/ethyl acetate = 3/2).

Yield: 0.2485 g (73.4%).

15-15) Preparation of methyl 7-[(1 R, 2 R, 3 R, 5 S)-2-(E-5,5-difluoro-4-oxo-2-octenyl)-5-hydroxy-3-(tetrahydropyranyloxy)cyclopentyl]heptanoate (69)

The alcohol (68) (0.2443 g) was treated with dimethyl (3,3-difluoro-2-oxohexyl)phosphonate (0.4915 g), 60% sodium hydride (0.0805 g) and zinc chloride (0.2743 g) in THF (15 ml) to give the $\alpha,\beta$-unsaturated ketone (69). The crude product obtained after the work-up was chromatographed on a column of silica gel (hexane/ethyl acetate = 2/1).

Yield: 0.1850 g (58.9%)

15-16) Preparation of methyl 7-[(1 R, 2 R, 3 R, 5 S)-2-(E-5,5-difluoro-4-oxo-2-octenyl)-5-oxo-3-(tetrahydropyranyloxy)cyclopentyl]heptanoate (70)

The $\alpha,\beta$-unsaturated ketone (69) (0.1800 g) was converted to the diketone (70) with Swern oxidation using oxalyl chloride (2-M, 0.42 ml) in dichloromethane (8 ml).

Yield: 0.1680 g (93.6%).

15-17) Preparation of methyl 7-[(1 R, 2 R, 3 R, 5 S)-2-(E-5,5-difluoro-4-oxo-2-octenyl)-3-hydroxy-5-oxocyclopentyl]heptanoate (71)

The diketone (70) (0.1680g) was kept in a mixed solvent of acetic acid, THF and water (3/1/1, 20 ml) at 50° C. for 3 hours. The crude product obtained after the work-up was chromatographed on a column of silica gel to give the title compound. (solvent)

Yield: 0.060 g (46.6%).

Compound (71) ($X_1 = X_2 = F$, $R_2$-$R_3$=propyl, A'=-methyl)

$^1$HMR (CDCl$_3$) $\delta$ : 0.99 (3H, t, J=7 Hz), 1.1–2.85 (22H, m), 3.67 (3H, s), 4.15 (1H, m), 6.62 (1H, d, J=15 Hz), 7.27 (1H, dt, J=15 Hz, 7.5 Hz)

MS m/z 402 (M$^+$), 384 (M$^+$=H$_2$O), 382(m$^+$-HF), 364 (M$^+$-HF-H$_2$O)

| Formulation Example 1 (Injectable solution) | |
|---|---|
| | Parts by weight |
| 15-dehydroxy-17,17-difluoro-13,14-dihydro-16-oxo-PGE$_2$ | 0.2 |
| nonion surfactant | 2 |
| sterile water for injection | 98 |

The above ingredients were mixed and sterilized to give a solution for injection.

| Formulation Example 2 (Powers for oral administration) | |
|---|---|
| | Parts by weight |
| 15-dehydroxy-17,17-difluoro-13,14-dihydro-16-oxo-PGE$_1$ | 5 |
| light anhydrous silicic acid | 5 |
| Abicel* | 20 |
| lactose | 70 |

The above ingredients were mixed to give powers for oral administration.

| Formulation Example 3 (Soft gelatin capsules) | |
|---|---|
| | Parts by weight |
| 15-dehydroxy-17,17-difluoro-13,14-dihydro-16-oxo-PGE$_1$ methyl ester | 1 |
| Panasate | 899 |

The above ingredients were mixed and filled into soft gelatin capsules.

| Formulation Example 4 (Injectable solution) | |
|---|---|
| | Parts by weight |
| 15-dehydroxy-17,17-difluoro-13,14-dihydro-16-oxo-PGF$_{2\alpha}$ methyl ester | 0.2 |
| nonion surfactant | 2 |
| sterile water for injection | 98 |

The above ingredients were mixed and sterilized to give a solution for injection.

| Formulation Example 5 (Ophthalmic solution) | |
|---|---|
| 15-dehydroxy-17,17-difluoro-13,14-dihydro-16-oxo-20-methyl-PGE$_2$ methyl ester | 10 mg |
| physiological saline | 10 ml |

The above ingredients were placed in separate vials. The vials were combined for preparing a solution on actual use.

TEST EXAMPLE 1

A guinea pig was sacrificed by knocking at the occipital region and then bleeding from the femoral artery. The trachea was removed, incised in the longitudinal direction at the opposite side of the smooth muscle and sectioned into sections of about 1 to 1.5 cm along the cartilage. Seven or eight sections were linked by a silk thread in chains. The sample was stretched by 1.0 g of tension in 15 ml of Tyrode's solution at 37° C under flow of the mixed gas of 95% $O_2$ and 5% $CO_2$. After resting for 60 to 90 minutes for stabilization, the sample was contracted with $5.4 \times 10^{-4}$M histamine and when the construction reached the constant value, the test compounds were accumulately added every 6 minutes, and the change in tension was recorded on a recorder (T-626DS, Nippon Denshi Kagaku, Japan) through an isometric transducer (1T-1, LABOX, Fukukensha, Japan).

Rate of inhibition by the test compounds of the contraction by histamine was expressed in percent, and $IC_{20}$ and $IC_{50}$ values were calculated as the concentration of the test compounds for 20% and 50% contraction, respectively. The results obtained are shown in Table 1.

TABLE 1

| Test Compound | $IC_{20}$ | $IC_{50}$ |
|---|---|---|
| 1 | $3 \times 10^{-7}$ M | $1.2 \times 10^{-6}$ M |
| 2 | $3 \times 10^{-7}$ M | $2 \times 10^{-6}$ M |
| 3 | $5 \times 10^{-7}$ M | $2 \times 10^{-6}$ M |
| 4 | $1 \times 10^{-5}$ M | — |
| 5 | $1.3 \times 10^{-7}$ M | $1.5 \times 10^{-6}$ M |
| 6 | $1 \times 10^{-7}$ M | $3.5 \times 10^{-7}$ M |
| 7 | $1.7 \times 10^{-5}$ M | — |

Test Compounds:
1: 13,14-dihydro-15-dehydroxy-16-oxo-17,17-difluoro-$PGE_2$ methyl ester
2: 13,14-dihydro-15-dehydroxy-16-oxo-17,17-difluoro-$PGE_2$
3: 13,14-dihydro-15-dehydroxy-16-oxo-17,17-difluoro-$PGE_2$ isopropyl ester
4: 13,14-dihydro-11,15-didehydroxy-11-methyl-16-oxo-17,17-difluoro-$PGE_2$ methyl ester
5: 13,14-dihydro-15-dehydroxy-16-oxo-17,17-difluoro-20-methyl-$PGE_2$ methyl ester
6: 13,14-dihydro-15-dehydroxy-16-oxo-17,17-difluoro-$PGE_1$ methyl ester
7: 13,14-dihydro-15-dehydroxy-16-oxo-17,17-difluoro-$PGF_{2\alpha}$ methyl ester

TEST EXAMPLE 2

A guinea pig was intraperitoneally anesthetized with 1.0–1.2 g/kg urethane (Katayama Kagaku, Japan). The test animal was cannulated through the common carotid vein and the trachea, and then pancuronium bromide was intravenously respiration of the test animal. The animal was artificially respired using a respirator for a small animal (SN-480-7, Shinano Seisakusho, Japan) and bronchospasm transducer (7020, Ugo Basile). The overflowing air at 6–9 ml(air)/time, 60 times/minutes and loading pressure of 10 cm $H_2O$ was recorded on a recorder (056-1001, Hitachi Seisakusho, Japan) through the bronchospasm transducer. Histamine (3 µg/kg) was administered several times at 30 minutes intervals, and when the increase in the airway resistance by histamine was established, the test compounds were intravenously administered one minute before the administration of histamine (3 µg/kg) to induce airway constriction. The difference of airway resistance before and after the administration of histamine was taken as 100% and activity of test compounds was shown in terms of percent inhibition of the increase due to histamine. The results are shown in Table 2.

TABLE 2

| Test Compound | Dose (µg/kg. i.v.) | Inhibition (%) |
|---|---|---|
| 1 | 10 | 92 |
| 2 | 10 | 78 |
| 5 | 5 | 84 |
| 6 | 5 | 93 |

Test Compounds 1,2,5 and 6: See Test Example 1.

TEST EXAMPLE 3

A guinea pig was sacrificed by knocking at the occipital region and then bleeding from the femoral artery. The trachea was removed, incised in the longitudinal direction at the opposite side of the smooth muscle and sectioned into sections of about 1 to 1.5 cm along the cartilage. Seven or eight sections were linked by a silk thread in chains. The sample was stretched by 1.0 g of tension in 15 ml of Tyrode's solution at 37° C. under flow of the mixed gas of 95% $O_2$ and 5% $CO_2$. After resting for 60 to 90 minutes for stabilization, the sample was contracted with $1 \times 10^{-8}$M leukotriene $D_4$ and when the construction reached the constant value, the test compounds were accumulately added every 6 minutes, and the change in tension was recorded on a recorder (T-626DS, Nippon Densi Kagaku, Japan) through an isometric transducer (1T-1, LABOX, Fukukensha, Japan).

Rate of inhibition by the test compounds of the contraction by leukotriene $D_4$ was expressed in percent, and $IC_{20}$ and $IC_{50}$ values were calculated as the concentration of the test compounds for 20% and 50% contraction, respectively. The results obtained are shown in Table 3.

TABLE 3

| Test Compound | $IC_{20}$ | $IC_{50}$ |
|---|---|---|
| 1 | $1.6 \times 10^{-7}$ M | $5 \times 10^{-7}$ M |
| 2 | $3 \times 10^{-7}$ M | $1 \times 10^{-6}$ M |
| 3 | $1.8 \times 10^{-7}$ M | $6 \times 10^{-7}$ M |
| 4 | $7 \times 10^{-6}$ M | $2.5 \times 10^{-5}$ M |
| 5 | $3 \times 10^{-7}$ M | $8 \times 10^{-8}$ M |
| 6 | $4 \times 10^{-8}$ M | $1.2 \times 10^{-7}$ M |
| 7 | $4 \times 10^{-6}$ M | $2 \times 10^{-5}$ M |

Test Compounds 1–7: See Test Example 1

TEST EXAMPLE 4

A guinea pig was intraperitoneally anesthetized with 1.2 g/kg urethane (Katayama Kagaku, Japan). The test animal was cannulated through the common carotid vein and the trachea, and then pancuronium bromide was intravenously administered at 0.3 mg/kg to stop the spontaneous respiration of the test animal. The animal was artificially respired using a respirator for a small animal (SN-480-7, Shinano Seisakusho, Japan) and bronchospasm transducer (7020, Ugo Basile). The overflowing air at 7–10 ml(air)/time, 60 times/minute and loading pressure of 10 cm $H_2O$ was recorded on a recorder (056-1001, Hitachi Seisakusho, Japan) through the bronchospasm transducer. When the base line was established, platelet activating factor (PAF) (50 ng/kg) was intravenously administered. The increase in the airway resistance was determined taking the value at the complete occlusion of trachea as the maximum contraction (100%). The test compounds were intravenously administered one minute before the administration of PAF. The difference of airway resistance before and after the administration of 50 ng/kg PAF was taken as 100% and activity of test compound was shown in terms of percent inhibition of the increase due to PAF. The results are shown in Table 4.

TABLE 4

| Test Compound | dose | n | Increase in Resistance (%, mean) | Inhibition (%) |
|---|---|---|---|---|
| —(control) | — | 2 | 74.5 | — |
| 6 | 10 µg/kg | 2 | 11.5 | 84.6 |

Test Compound 6: See Test Example 1.

TEST EXAMPLE 5

A guinea pig was intraperitoneally anesthetized with 1.0-1.2 g/kg urethane (Katayama Kagaku, Japan). The test animal was cannulated through the common carotid vein and the trachea, and then pancuronium bromide was intravenously administered at 0.3 mg/kg to stop the spontaneous respiration of the test animal. The animal was artificially respired using a respirator for a small animal (SN-480-7, Shinano Seisakusho, Japan) and bronchospasm transducer (7020, Ugo Basile). The overflowing air at 6-9 ml(air)/time, 60 times/minute and loading pressure of 10 cm $H_2O$ was recorded on a recorder (056-1001, Hitachi Seisakusho, Japan) through the bronchospasm transducer. Histamine (3 $\mu$g/kg) was administered several times at 30 minutes intervals, and when the maximum airway constriction by histamine was established, a solution of the test compound (10$\mu$g/ml), atomized by an ultrasonic nebulizer (NE-U10B, Tateishi Denki, Japan) was given by artificial inhalation for 2 minutes (52.4 ng in total) one minute before the administration of histamine (3 $\mu$g/kg) to induce airway constriction. The increase in airway resistance was determined taking the value at the complete occlusion of trachea as the maximum contraction (100%). The activity of test compound was shown in terms of percent inhibition of the increase (to be taken as 100%) due to histamine (3 $\mu$g/kg). The results are shown in Table 5.

TABLE 5

| Test Compound | Concentration | n | Increase in Resistance (%, mean) | Inhibition (%) |
|---|---|---|---|---|
| — | — | 2 | 62.5 | — |
| 6 | 10 $\mu$g/ml | 2 | 11.0 | 84.0 |

Test Compound 6: See Test Example 1.

TEST EXAMPLE 6

Female Wistar rats (weight: 90 g) were used as the test animals. The animals received the test compounds and, 3 minutes after, 0.5ml of 0.5% Ebans Blue/physiological saline was administered through the caudal vein. Then, immediately after, 0.05ml of 0.1% histamine hydrochloride/physiological saline was injected subconjunctivally at an upper eyelid. After 30 minutes, the animals were sacrificed by vertebral cervial dislocation and the scalp was peeled away towards the eyelid. Part of skin and conjunctive showing inflammation was cut off and weighed. Then, said conjunctive was minced and extracted overnight with 4 ml formaldehyde at 40° C. with shaking. The dye in the conjunctive was assayed by measuring absorption of the extract at 625 nm. The administration of the test compounds was carried out by ophthalmically administering a solution of each of the compounds (5$\mu$g/eye) in the physiological saline. Control animals received the same amount of the physiological saline. The results are shown in Table 6.

TABLE 6

| Test Compound | Dose ($\mu$g) | n (eye) | Weight of Conjunctive (Mean ± S.D.)(mg) | Dye ($\mu$g/part) |
|---|---|---|---|---|
| — (control) | 0 | 16 | 41.5 ± 2.0 | 8.26 ± 0.52 |
| 1 | 3 | 16 | 36.3 ± 2.1 | 7.13 ± 0.65 |
| 6 | 3 | 16 | 32.7 ± 1.8** | 5.95 ± 0.53* |
| 8 | 3 | 14 | 38.5 ± 2.0 | 7.69 ± 0.71 |
| 9 | 3 | 14 | 38.9 ± 1.8 | 7.49 ± 0.67 |

DUNNET test *P < 0.05, **P < 0.01
Test Compounds 1 and 6: See Test Example 1.
8: 13,14-dihydro-15-dehydroxy-16-oxo-17,17-difluoro-$PGD_2$ methyl ester
9: 13,14-dihydro-15-dehydroxy-16-oxo-17,17-difluoro-$PGA_2$ methyl ester

TEST EXAMPLE 7

Male Crj Wistar rats (7 weeks old) were passively sensitized by injecting 50$\mu$l of diluted rat anti-EA (egg albumin) antiserum at the dorsal skin.

After 48 hours, 1 ml of a mixture consisting of equal amount of 1% EA (egg albumin) as the antigen in physiological saline and 1% Evans Blue in physiological saline was injected in the caudal vein to elicit the PCA reaction. After 30 minutes, the animals were killed by deep anesthetization and dorsal skin was ablated. The major and minor axes of reacted part, i.e. pigment-leaking site were measured and the average value of them was taken as the diameter, from which the area was calculated.

Then said site was punched and amount of the pigment was measured by the following method.

The punched site was dipped in 1 ml of 1 N aqueous potassium hydroxide and allowed to stand overnight at 37° C. then 9ml of a mixed solution of 0.6 N $H_3PO_4$: acetone (5:13) was added and the mixture was centrifuged. The supernatant was assayed for absorption at 620 nm using an absorption spectrophotometer. The amount of the pigment was determined by calibration curve which was obtained using the known amounts of the pigment.

The test compound was dissolved in the physiological saline and intravenously administered. The control animals intravenously received the physiological saline (5 ml/kg) alone.

The results are shown in Table 7.

TABLE 7

| Compound | Dose ($\mu$g/kg) | Animal (n) | Area (mm$^2$) | Amount ($\mu$g/site) |
|---|---|---|---|---|
| Control | — | 20 | 56.9 ± 19.4 | 104.9 ± 45.4 |
| 6 | 10 | 16 | 33.7 ± 7.5 | 38.0 ± 15.9 |

Test Compound: See Test Example 1.

It can be clearly seen from the above results that the test compounds have a strong antagonistic activity against histamine, leukotriene and platelet activating factor (PAF), typical allergy- and inflammation-inducing substances.

TEST EXAMPLE 8

The procedure of Test Example 2 was repeated except that Test Compound 10 (15-dehydroxy-17,17-difluoro-13,14-dihydro-14,15-didehydro-16-oxo-$PGE_1$ methyl ester) was used.

TABLE 8

| Test Compound | Dose ($\mu$g/kg, i.v.) | Inhibition (%) |
|---|---|---|
| 10 | 3 | 72.7% |
| 10 | 10 | 93.6% |

TEST EXAMPLE 9

The procedure of Test Example 5 was repeated except that Test Compound 10 (15-dehydroxy-17,17-difluoro-13,14-dihydro-14,15-didehydro-16-oxo-PGE$_1$ methyl ester) was used.

TABLE 9

| Test Compound | Concentration (μg/ml) | n | Increase in Resistance (Mean ± S.E.) | Inhibition (%) (Mean ± S.E.) |
|---|---|---|---|---|
| Control | — | 4 | 68.9 ± 7.3 | — |
| 10 | 10 | 4 | 15.2 ± 2.6** | 77.8 ± 3.0** |

DUNNET test **P < 0.01

What we claim is:

1. A method for treatment of an allergic disease which comprises administering, to a subject in need of such treatment, a 15-dehydroxy-16-oxoprostaglandin compound in an amount effective in treatment of the allergic disease.

2. A method according to claim 1, wherein said 15-dehydroxy-16-oxoprostaglandin compound is a 17-mono- or di-halo-15-dehydroxy-16-oxoprostaglandin compound.

3. A method according to claim 1, wherein said 15-dehydroxy-16-oxoprostaglandin compound is a 13,14-dihydro-17-mono or di-halo-15-dehydroxy-16-oxoprostaglandin compound.

4. A method according to claim 1, wherein said 15-dehydroxy-16-oxoprostaglandin compound is a 13,14-dihydro-17-mono or di-fluoro-15-dehydroxy-16-oxoprostaglandin compound.

5. A method for treatment of an inflammatory disease which comprises administering, to a subject in need of such treatment, a 15-dehydroxy-16-oxoprostaglandin compound in an amount effective in treatment of the inflammatory disease.

6. A method according to claim 5, wherein said 15-dehydroxy-16-oxoprostaglandin compound is a 17-mono- or di-halo-15-dehydroxy-16-oxoprostaglandin compound.

7. A method according to claim 5, wherein said 15-dehydroxy-16-oxoprostaglandin compound is a 13,14-dihydro-17-mono or di-halo-15-dehydroxy-16-oxoprostaglandin compound.

8. A method according to claim 5, wherein said 15-dehydroxy-16-oxoprostaglandin compound is a 13,14-dihydro-17-mono or di-fluoro-15-dehydroxy-16-oxoprostaglandin compound.

9. A method for treatment of a disease treatable by a antihistaminic agent which comprises administering, to a subject in need of such treatment, an antihistaminically effective amount of a 15-dehydroxy-16-oxoprostaglandin compound.

10. A method according to claim 9, wherein said 15-dehydroxy-16-oxoprostaglandin compound is a 17-mono- or di-halo-15-dehydroxy-16-oxoprostaglandin compound.

11. A method according to claim 9, wherein said 15-dehydroxy-16-oxoprostaglandin compound is a 13,14-dihydro-17-mono or di-halo-15-dehydroxy-16-oxoprostaglandin compound.

12. A method according to claim 9, wherein said 15-dehydroxy-16-oxoprostaglandin compound is a 13,14-dihydro-17-mono or di-fluoro-15-dehydroxy-16-oxoprostaglandin compound.

13. A method for treatment of a disease treatable by a leukotriene antagonist which comprises administering, to a subject in need of such treatment, a 15-dehydroxy-16-oxoprostaglandin compound in an amount effective in antagonism against a leukotriene.

14. A method according to claim 13, wherein said 15-dehydroxy-16-oxoprostaglandin compound is a 17-mono- or di-halo-15-dehydroxy-16-oxoprostaglandin compound.

15. A method according to claim 13, wherein said 15-dehydroxy-16-oxoprostaglandin compound is a 13,14-dihydro-17-mono or di-halo-15-dehydroxy-16-oxoprostaglandin compound.

16. A method according to claim 13, wherein said 15-dehydroxy-16-oxoprostaglandin compound is a 13,14-dihydro-17-mono or di-fluoro-15-dehydroxy-16-oxoprostaglandin compound.

17. A method for treatment of a disease treatable by a platelet activating factor antagonist which comprises administering, to a subject in need of such treatment, a 15-dehydroxy-16-oxoprostaglandin compound in an amount effective in antagonist against the platelet activating factor.

18. A method according to claim 17, wherein said 15-dehydroxy-16-oxoprostaglandin compound is a 17-mono- or di-halo-15-dehydroxy-16-oxoprostaglandin compound.

19. A method according to claim 17, wherein said 15-dehydroxy-16-oxoprostaglandin compound is a 13,14-dihydro-17-mono or di-halo-15-dehydroxy-16-oxoprostaglandin compound.

20. A method according to claim 17, wherein said 15-dehydroxy-16-oxoprostaglandin compound is a 13,14-dihydro-17-mono or di-fluoro-15-dehydroxy-16-oxoprostaglandin compound.

21. A method for treatment of a disease treatable by bronchodilatation which comprises administering, to a subject in need of such treatment, a 15-dehydroxy-16-oxoprostaglandin compound in an amount effective in causing bronchodilatation.

22. A method according to claim 21, wherein said 15-dehydroxy-16-oxoprostaglandin compound is a 17-mono- or di-halo-15-dehydroxy-16-oxoprostaglandin compound.

23. A method according to claim 21, wherein said 15-dehydroxy-16-oxoprostaglandin compound is a 13,14-dihydro-17-mono or di-halo-15-dehydroxy-16-oxoprostaglandin compound.

24. A method according to claim 21, wherein said 15-dehydroxy-16-oxoprostaglandin compound is a 13,14-dihydro-17-mono or di-fluoro-15-dehydroxy-16-oxoprostaglandin compound.

25. A method according to claim 1, wherein said 15-dehydroxy-16-oxoprostaglandin compound is represented by the following formula:

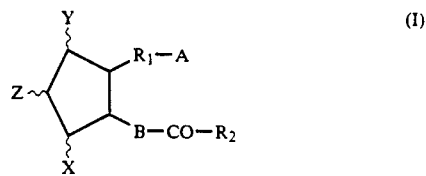

wherein X and Y ar hydrogen, hydroxy, halo, lower alkyl, hydroxy(lower)alkyl or oxo, with the proviso that a least one of X and Y is a group other than hydrogen, and 5-membered ring may have at least one double bond, Z is hydrogen or halo, A is—$CH_2OH$, —$COCH_2OH$, —COOH or its functional derivative, B is —$CH_2$—$CH_2$—$CH_2$—, —CH=CH—$CH_2$—, —$CH_2$—CH=CH—, —C≡C—$CH_2$—or —$CH_2$—C≡C—, $R_1$ is a bivalent saturated or unsaturated, straight or blanched chain hydrocarbyl group having 1 to 14 carbon atoms which is unsubstituted or substituted with halo, oxo, or aryl, $R_2$ is a saturated or unsaturated, straight or branched chain hydrocarbyl group having 1 to 14 carbon atoms which is unsubstituted or substituted with halo, hydroxy, oxo, lower alkoxy, aryl or aryloxy.

26. A method according to claim 25, wherein X is hydroxy and Y is oxo.

* * * * *